(12) United States Patent
Ie et al.

(10) Patent No.: US 10,688,318 B2
(45) Date of Patent: Jun. 23, 2020

(54) RADIOGRAPHIC IMAGING APPARATUS AND PARTICLE BEAM THERAPY SYSTEM

(71) Applicant: Hitachi, Ltd., Tokyo (JP)

(72) Inventors: Shinichirou Ie, Tokyo (JP); Norihiro Uemura, Tokyo (JP); Keigo Takeuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 491 days.

(21) Appl. No.: 15/604,841

(22) Filed: May 25, 2017

(65) Prior Publication Data

US 2017/0340903 A1 Nov. 30, 2017

(30) Foreign Application Priority Data

May 31, 2016 (JP) ................................ 2016-109092

(51) Int. Cl.
*A61B 5/00* (2006.01)
*A61N 5/10* (2006.01)
*A61B 6/06* (2006.01)
*A61B 6/00* (2006.01)
*A61B 6/03* (2006.01)

(52) U.S. Cl.
CPC ............ *A61N 5/1049* (2013.01); *A61B 6/032* (2013.01); *A61B 6/06* (2013.01); *A61B 6/4014* (2013.01);
(Continued)

(58) Field of Classification Search
CPC ................ A61N 5/1049; A61N 5/1081; A61N 2005/1087; A61N 2005/1061;
(Continued)

(56) References Cited

U.S. PATENT DOCUMENTS 5,993,373 A 11/1999 Nonaka et al.
2004/0258195 A1 12/2004 Hara
(Continued)

FOREIGN PATENT DOCUMENTS

JP 11-047287 A 2/1999
JP 2005-006772 A 1/2005
(Continued)

OTHER PUBLICATIONS

Extended European Search Report received in corresponding European Application No. 17173021.1 dated Nov. 7, 2017.

*Primary Examiner* — Joel Lamprecht
(74) *Attorney, Agent, or Firm* — Mattingly & Malur, PC

(57) ABSTRACT

The radiographic imaging apparatus is configured so that an irradiation device is mounted on a rotary drum of a rotary gantry. A pair of X-ray sources is disposed outside the rotary drum and attached to the outer surface of the rotary drum. A pair of FPDs facing the respective X-ray sources is mounted in the irradiation device. When X-rays are irradiated, X-ray intensity information is calculated by a signal processing device based an output signal from each radiation detection element of each FPD, and stored in a memory. Based on FOV information set by an input device, an X-ray intensity acquisition device acquires multiple pieces of X-ray intensity information that are calculated based on the output signals from the radiation detection elements in small FOV areas (or large FOV areas) of the FPDs, which are included in the X-ray intensity information stored in the memory.

12 Claims, 23 Drawing Sheets

(52) U.S. Cl.
CPC .......... *A61B 6/4452* (2013.01); *A61B 6/5205* (2013.01); *A61N 5/1081* (2013.01); *A61B 6/4085* (2013.01); *A61B 6/4266* (2013.01); *A61N 2005/1061* (2013.01); *A61N 2005/1087* (2013.01)

(58) Field of Classification Search
CPC .... A61N 2005/1092; A61N 2005/1054; A61N 5/1077; A61N 5/1071; A61N 5/1048; A61N 5/1047; A61N 5/1027; A61B 6/4014; A61B 6/06; A61B 6/5205; A61B 6/4452; A61B 6/032; A61B 6/4266; A61B 6/4085; A61B 6/54; A61B 6/4275; A61B 6/40

See application file for complete search history.

(56) References Cited

U.S. PATENT DOCUMENTS

| | | |
|---|---|---|
| 2006/0163495 A1 | 7/2006 | Hiramoto et al. |
| 2015/0043715 A1 | 2/2015 | Kuwabara et al. |
| 2017/0001041 A1* | 1/2017 | Yamashita ........... A61N 5/1049 |
| 2017/0231583 A1* | 8/2017 | Goteti Venkata ........ A61B 6/03 600/427 |

FOREIGN PATENT DOCUMENTS

| | | |
|---|---|---|
| JP | 2006-239403 A | 9/2006 |
| JP | 2014-006235 A | 1/2014 |
| WO | 2016/030772 A1 | 3/2016 |

* cited by examiner

RADIOGRAPHIC IMAGING APPARATUS AND PARTICLE BEAM THERAPY SYSTEM

CLAIM OF PRIORITY

The present application claims priority from Japanese patent application JP 2016-109092 filed on May 31, 2016, the content of which is hereby incorporated by reference into this application.

BACKGROUND OF THE INVENTION

(1) Field of the Invention

The present invention relates to a radiographic imaging apparatus and to a particle beam therapy system. In particular, the present invention relates to a radiographic imaging apparatus suitable, for example, for a proton beam therapy system that provides cancer therapy by using a proton beam, which is a particle beam categorized as radiation, and also relates to a particle beam therapy system suitable as a proton beam therapy system.

(2) Description of the Related Art

A particle beam therapy system is used, for example, for cancer therapy. The particle beam therapy system irradiates a particle beam (proton beam or heavy particle beam (carbon ion beam, etc.)) that matches the position and shape of a diseased part.

The particle beam therapy system is roughly classified into two well-known types. One of them uses a synchrotron as an accelerator, and the other uses a cyclotron as an accelerator. The particle beam therapy system having the synchrotron and the particle beam therapy system having the cyclotron both include a rotary gantry that is equipped with an irradiation device.

In order to efficiently provide particle beam therapy, it is necessary to accurately irradiate a cancer-affected part of a patient with a particle beam. Therefore, a particle beam therapy system structured to be capable of placing the irradiation device in an optimal irradiation position for the patient has been developed. To enable such a particle beam therapy system to provide particle beam therapy in a desired direction from all sides of the patient, it is necessary to use a rotary gantry capable of rotating 360 degrees around the patient and a radiotherapy cage (hereinafter referred to as the therapy cage) operating in synchronism with the rotation of the rotary gantry.

An example of the rotary gantry with the therapy cage is described in Japanese Patent Application Laid-Open No. Hei 11 (1999)-47287. The therapy cage includes a stationary ring rail, a rotary ring rail, and a movable floor. The stationary ring rail and the rotary ring rail are disposed inside the rotary gantry and attached to the rotary gantry. The stationary ring rail and the rotary ring rail form a semicylindrical track on their opposing surfaces in order to guide the movable floor. The movable floor includes many footboards that are flexibly coupled to each other by a link, and moves along the semicylindrical track in synchronism with the rotation of the rotary gantry. This causes some footboards of the movable floor to form a horizontal floor (access floor). Within the therapy cage, healthcare personnel (e.g., a doctor and a medical technologist) can stand on the horizontal floor and easily access a patient on a treatment table inserted into the therapy cage.

A technology described in Japanese Patent Application Laid-Open No. 2006-239403 calculates the movement amount of a bed and the rotation angle of the bed, and allows a bed control device to automatically position a diseased part with respect to an irradiation device based on the calculated movement amount and rotation angle. The technology described in Japanese Patent Application Laid-Open No. 2006-239403 allows an X-ray source in the irradiation device attached to the rotary gantry to irradiate X-rays while rotating the rotary gantry, permits an X-ray detection device to detect X-rays transmitted through a patient on a treatment table, and generates current tomographic image information by using an output signal of the X-ray detection device. The patient is positioned by using the current tomographic image information as well as reference tomographic image information about the diseased part that is obtained by preceding X-ray CT imaging.

Japanese Patent Application Laid-Open No. 2005-6772 describes an X-ray diagnostic apparatus that uses a flat-panel detector (FPD) as a radiation detection device. The X-ray diagnostic apparatus performs CT imaging by rotating an X-ray source around a patient on a bed, which is an examination subject, allowing the X-ray source to irradiate X-rays, and permitting the FPD to detect the X-rays transmitted through the body of the patient. The X-ray diagnostic apparatus performs CT imaging of a small field-of-view (hereinafter referred to as the small FOV) or CT imaging of a large field-of-view (hereinafter referred to as the large FOV) depending on whether the head or trunk of the patient is an X-ray radiation target.

For small FOV CT imaging of the head, a collimator is adjusted so that X-rays emitted from the X-ray source fall within the small FOV while the X-ray source, the body axis of the patient, and the detection surface of the FPD are in alignment. The X-rays emitted from the X-ray source and transmitted through the collimator are then allowed to fall on the head of the patient while the X-ray source, which emits X-rays toward the head, and the FPD, which detects the X-rays transmitted through the head, are rotating around the head. Further, for large FOV CT imaging of the trunk, the FPD is moved in a direction perpendicular to a straight line connecting the X-ray source to the body axis of the patient, and then the collimator is adjusted so that the X-rays emitted from the X-ray source fall within the large FOV while the X-ray source, the body axis of the patient, and the left edge of the detection surface of the FPD are in alignment. Next, while the X-ray source, which emits X-rays toward the trunk, and the FPD, which detects X-rays transmitted through the trunk, are rotated around the trunk, the X-rays emitted from the X-ray source and transmitted through the collimator are allowed to fall on the trunk of the patient. As the FPD is moved in the aforementioned perpendicular direction before large FOV CT imaging, the FPD used for small FOV CT imaging and large FOV CT imaging can be made compact.

A radiographic imaging apparatus described in Japanese Patent Application Laid-Open No. 2014-6235 is configured so that TFT switches arranged in a matrix form are respectively connected to photodiodes that are provided for an indirect conversion FPD and arranged in a matrix form.

SUMMARY OF THE INVENTION

According to Japanese Patent Application Laid-Open No. 2005-6772, it is necessary to move the FPD so as to provide a small FOV when performing small FOV CT imaging, and move the FPD so as to provide a large FOV when performing large FOV CT imaging.

Therefore, the X-ray diagnostic apparatus described in Japanese Patent Application Laid-Open No. 2005-6772 needs to incorporate an FPD transport device for moving the FPD, a control device for controlling the movement of the FPD transport device, and a monitoring device for monitoring whether the FPD is moved and set at a predetermined position. Consequently, the X-ray diagnostic apparatus has a complex structure.

In consideration of such a complex structure of the X-ray diagnostic apparatus, the inventors of the present invention conducted studies on structural simplification of a radiographic imaging apparatus for use in a particle beam therapy system that is capable of acquiring three-dimensional tomographic image information for patient positioning by irradiating a patient on a bed with X-rays while rotating a rotary gantry.

The present invention has been made to provide a radiographic imaging apparatus and a particle beam therapy system that both have a simplified structure.

According to an aspect of the present invention, there is provided a radiographic imaging apparatus including a rotating body, an X-ray generation device, a collimator, a radiation detection device, an input device, an X-ray intensity information generation device, and an image reconstruction device. The rotating body rotates around a bed. The X-ray generation device is mounted on the rotating body. The collimator is disposed in front of the X-ray generation device to form an aperture through which X-rays from the X-ray generation device pass. The radiation detection device is mounted on the rotating body so as to face the X-ray generation device and equipped with multiple radiation detection elements for detecting X-rays passing through the aperture of the collimator. The input device inputs either first imaging mode information or second imaging mode information. The first imaging mode information concerns a first irradiation area. The second imaging mode information concerns a second irradiation area that is larger than the first irradiation area. The X-ray intensity information generation device generates multiple pieces of X-ray intensity information about a selected FOV area of the radiation detection device based on an output signal of each radiation detection element in the selected FOV area either when a first FOV area of the radiation detection device that is symmetrical in the circumferential direction of the rotating body with respect to a second straight line passing through a point of intersection between the radiation detection device and a first straight line passing through a rotation center of the rotating body from the X-ray generation device and extended in the direction of the rotation axis of the rotating body is selected based on the first imaging mode information inputted from the input device, or when a second FOV area of the radiation detection device that is not circumferentially symmetrical with respect to the second straight line passing through the point of intersection is selected based on the second imaging mode information inputted from the input device. The image reconstruction device generates three-dimensional tomographic image information about a radiation target by using the multiple pieces of X-ray intensity information generated by the X-ray intensity information generation device.

If either the first imaging mode information concerning the first irradiation area or the second imaging mode information concerning the second irradiation area, which is larger than the first irradiation area, is inputted from the input device, the X-ray intensity information generation device generates multiple pieces of X-ray intensity information about a selected FOV area of the radiation detection device based on an output signal of each radiation detection element in the selected FOV area either when the first FOV area of the radiation detection device that is symmetrical in the circumferential direction of the rotating body with respect to the second straight line passing through the point of intersection with the radiation detection device and the first straight line passing through the rotation center of the rotating body from the X-ray generation device and extended in the direction of the rotation axis of the rotating body is selected based on the first imaging mode information inputted from the input device, or when the second FOV area of the radiation detection device that is not circumferentially symmetrical with respect to the second straight line passing through the point of intersection is selected based on the second imaging mode information inputted from the input device.

Consequently, the multiple pieces of X-ray intensity information generated based on output signals of the radiation detection elements in the first FOV area of the radiation detection device and the multiple pieces of X-ray intensity information generated based on output signals of the radiation detection elements in the second FOV area of the radiation detection device can be acquired without moving the radiation detection device. This eliminates the necessity of incorporating various devices for moving the radiation detection device. As a result, the structure of a particle beam therapy system can be simplified.

The structure of the radiographic imaging apparatus is simplified. The structure of the particle beam therapy system can also be simplified.

BRIEF DESCRIPTION OF THE DRAWINGS

Embodiments of the present invention will be described in detail based on the following figures, in which.

DETAILED DESCRIPTION OF THE INVENTION

Embodiments of the present invention will now be described.

First Embodiment

A particle beam therapy system 1 according to a first embodiment, which is a preferred embodiment of the present invention, is described below with reference to FIGS. 1 to 4.

Figure 1:
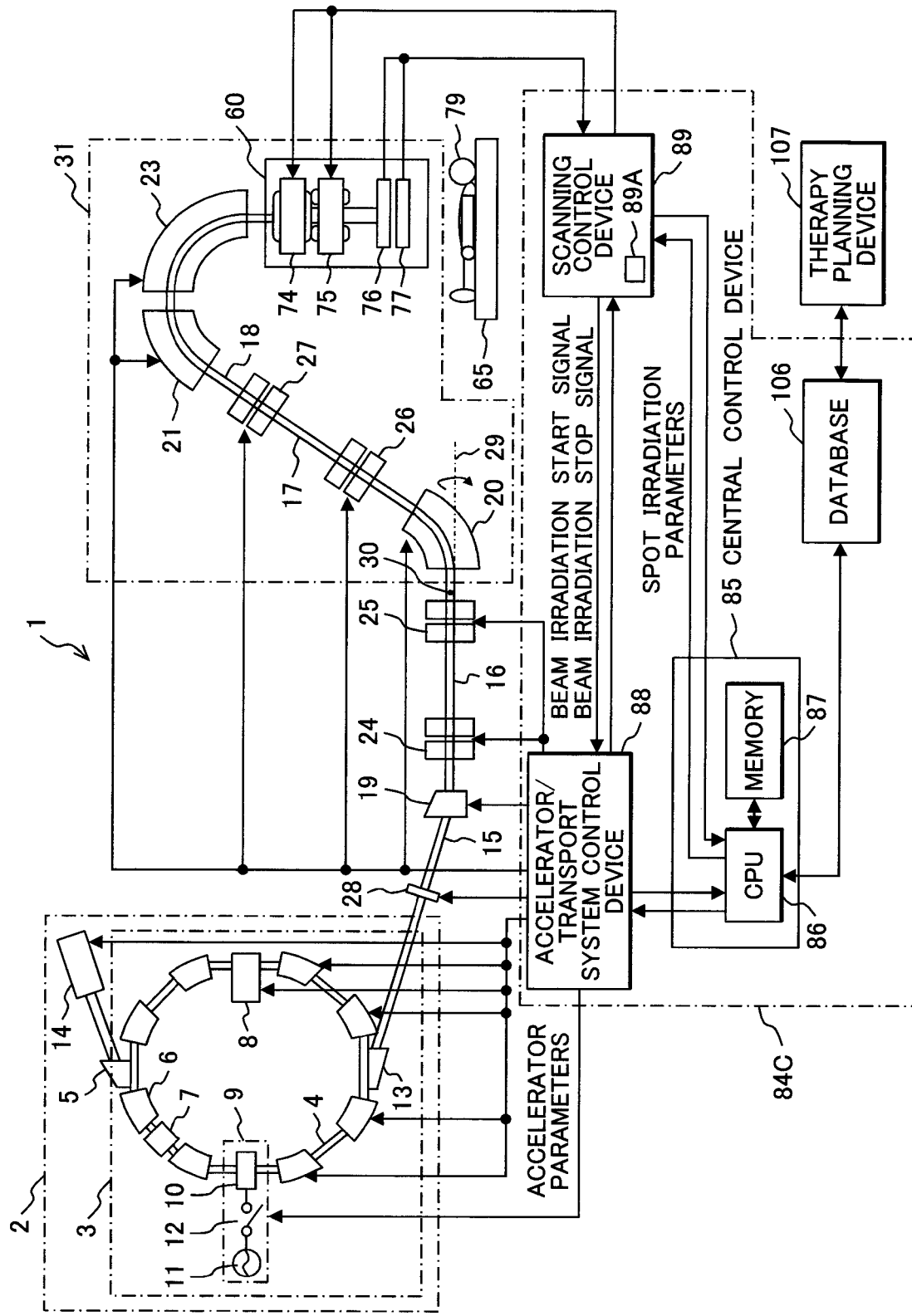
FIG. 1 is a diagram illustrating a configuration of a particle beam therapy system according to a first embodiment, which is a preferred embodiment of the present invention.

The particle beam therapy system 1 according to the present embodiment is disposed in a building (not shown) and mounted on a floor 71 (see FIG. 2) of the building. As illustrated in FIG. 1, the particle beam therapy system 1 includes an ion beam generation device 2, a high-energy beam transport system (HEBT system) 15, a gantry beam transport system (GABT system) 17, a rotary gantry 31, an irradiation device 60, and a control system 84C. The particle beam therapy system 1 uses a proton ion beam as the ion beam to be irradiated onto a cancer-affected part (radiation target). A carbon ion beam may be used instead of the proton ion beam.

The ion beam generation device 2 includes an ion source (not shown), a linear accelerator 14, and a synchrotron accelerator 3. The linear accelerator 14 acts as a preceding accelerator. The synchrotron accelerator 3 includes a beam duct 4, an injector 5, a high-frequency acceleration cavity (high-frequency acceleration device) 8, deflection electromagnets 6, quadrupole electromagnets 7, a high-frequency application device 9 for ejection, and a septum electromagnet 13 for ejection. The bean duct 4 has a circular shape and forms an ion beam orbit. The high-frequency acceleration cavity 8 applies a high-frequency voltage to the ion beam. The injector 5, which communicates with the beam duct 4, is connected to the linear accelerator 14 through a vacuum duct. The ion source is also connected to the linear accelerator 14. The high-frequency application device 9 includes an ejection high-frequency electrode 10, a high-frequency power supply 11, and an open/close switch 12. The ejection high-frequency electrode 10 is mounted on the beam duct 4 and connected to the high-frequency power supply 11 through the open/close switch 12. The deflection electromagnets 6, the quadrupole electromagnets 7, the high-frequency acceleration cavity 8, and the septum electromagnet 13 are disposed along the beam duct 4 as illustrated in FIG. 1.

The HEBT system (first beam transport system) 15 includes a beam path (beam duct) 16 that is connected to the septum electromagnet 13 of the synchrotron accelerator 3. A shutter 28, a deflection electromagnet 19, and quadrupole electromagnets 24, 25 are disposed along the beam path 16 from the synchrotron accelerator 3 to the irradiation device 60.

The GABT system (second beam transport system) 17 includes a beam path (beam duct) 18. A deflection electromagnet 20, quadrupole electromagnets 26, 27, and deflection electromagnets 21, 23 are disposed along the beam path 18 from the synchrotron accelerator 3 to the irradiation device 60. The beam path 18 and electromagnets of the GABT system 17 are attached to the rotary gantry 31. The beam path 18 communicates with the beam path 16 at an interface 30 between the HEBT system 15 and the GABT system 17. The beam path 18 is rotated by the rotary gantry 31, and is therefore not directly connected to the beam path 16.

The irradiation device 60 includes two scanning electromagnets (ion beam scanning device) 74, 75, a beam position monitor 76, and a dose monitor 77. The irradiation device 60 is mounted on the rotary gantry 31 and disposed downstream of the deflection electromagnet 23. In the irradiation device 60, the scanning electromagnets 74, 75, the beam position monitor 76, and the dose monitor 77 are disposed along the central axis 78 of the irradiation device 60 from the deflection electromagnet 23 to the ion beam exit of the irradiation device 60. The scanning electromagnet 74 deflects an ion beam in a plane perpendicular to the central axis 78 of the irradiation device 60 and performs scanning in the X-direction. The scanning electromagnet 75 deflects the ion beam in the same plane and performs scanning in the Y-direction, which is orthogonal to the X-direction. A treatment table 64

(see FIG. 2) on which a patient 79 lies is disposed to face the tip of the irradiation device 60.

The rotary gantry 31 will now be described with reference to FIGS. 2 and 3. The rotary gantry 31 includes a cylindrical rotary drum 32 having a front ring 33 and a rear ring 34, which are both ring-shaped. The front ring 33 is supported by a support device 35A mounted on the floor 71 of the building. The rear ring 34 is supported by a support device 35B mounted on the floor 71. The support device 35A includes a pair of roll support members 36 and multiple support rollers 37A. The support rollers 37A are rotatably mounted on the roll support members 36. The front ring 33 is supported by these support rollers 37A. As is the case with the support device 35A, the support device 35B includes a pair of roll support members 36 (not shown) and multiple support rollers 37B. The support rollers 37B are rotatably mounted on the roll support members 36. The rear ring 34 is supported by these support rollers 37B. The rotary shaft of a rotation device (e.g., a motor) that rotates the rotary gantry 31 is coupled to the rotary shaft of one of the support rollers 37B, which support the rear ring 34 through a speed reduction device 53. An angle detector 54A for measuring the rotation angle of the rotary gantry 31 is coupled to the rotary shaft of one of the support rollers 37A, which support the front ring 33.

Figure 18:
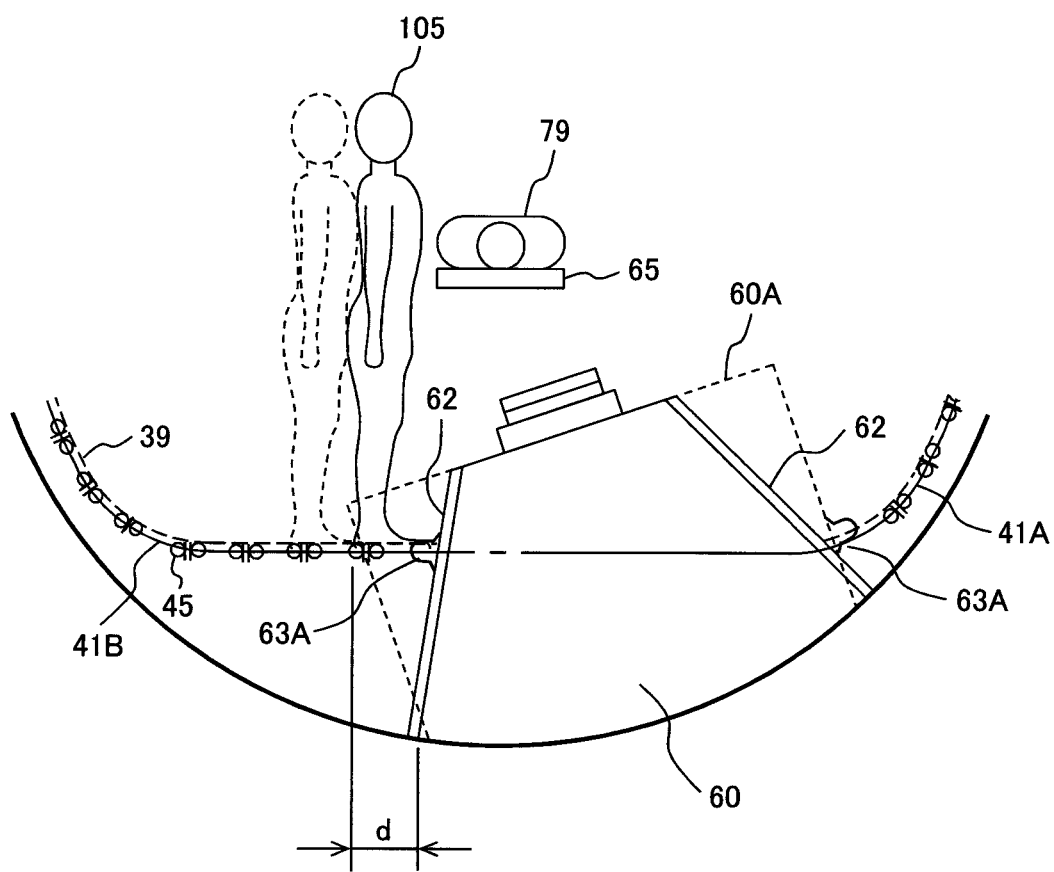
FIG. 18 is a diagram illustrating how a patient on the treatment table can be accessed by healthcare personnel on a horizontal floor of the particle beam therapy system according to the first embodiment.

A radiotherapy cage (therapy cage) 38 is disposed in the rotary gantry 31. The therapy cage is configured to assure the safety of the patient 79 on the treatment table 64 from a circumferential rotation path of the rotary gantry 31 in the irradiation device 60 and permit, for example, a medical technologist 105 (see the later-mentioned FIG. 18) to perform a medical action on the patient 79. That is to say, the therapy cage 38 provides a foothold for medical actions of the medical technologist 105. In other respects, however, it is desirable that the therapy cage 38 provide a closed space isolated from the surroundings.

The therapy cage 38 includes a movable floor 39, a stationary ring rail 48A, a movable ring rail 48B, and a rear panel 49. At the position of the front ring 33, the stationary ring rail 48A is disposed inside the front ring 33. The movable ring rail 48B faces the stationary ring rail 48A, and is disposed inside the rotary drum 32 and toward the rear ring 34. The irradiation device 60 is disposed between the stationary ring rail 48A and the movable ring rail 48B. The rear panel 49, which stops the deep side of the therapy cage 38, is secured to the movable ring rail 48B. The stationary ring rail 48A and the movable ring rail 48B form a semicylindrical track 102 (see FIG. 11) on their opposing surfaces. In the present embodiment, the shape of the semicylindrical track 102 includes an upper arc portion and a lower horizontal portion in such a manner that opposite ends of the arc portion are smoothly coupled to opposite ends of the horizontal portion. A portion where the arc portion is coupled to the horizontal portion is referred to as the coupling portion.

Figure 4:
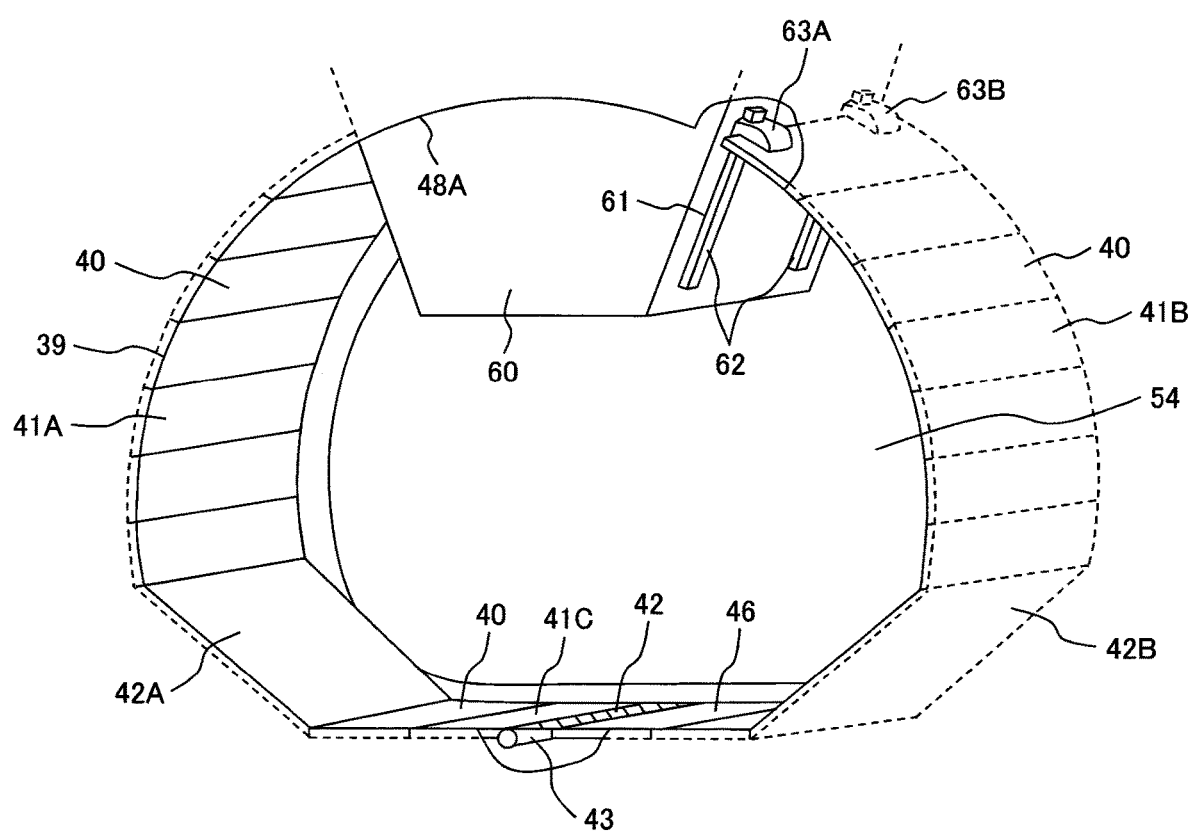
FIG. 4 is an enlarged perspective view of a radiotherapy cage shown in FIGS. 2 and 3.
Figure 5:
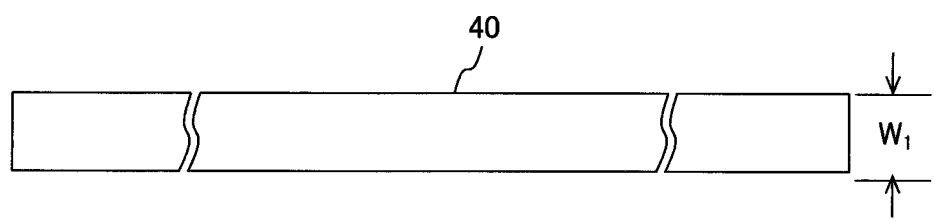
FIG. 5 is a plan view of a footboard shown in FIG. 4.
Figure 6:
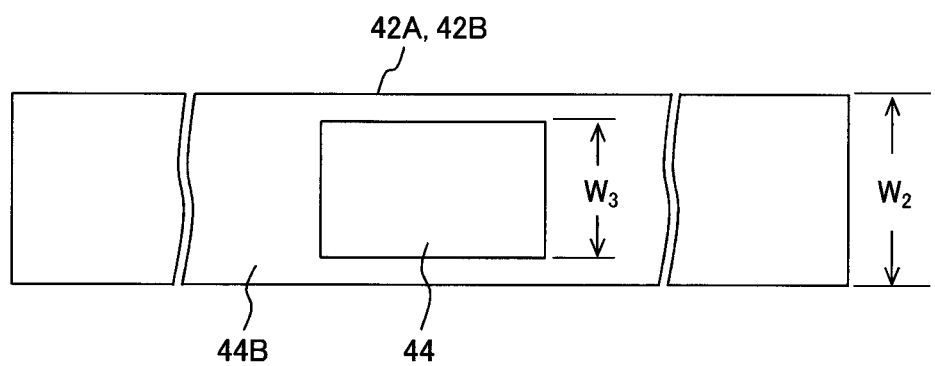
FIG. 6 is a plan view of an X-ray transmission plate shown in FIG. 4.

As illustrated in FIG. 4, the movable floor 39 includes many footboards (footboard members) 40, which is formed of a steel plate or other metal plate, and two X-ray transmission plates (X-ray transmission members) 42A, 42B, and is disposed between the stationary ring rail 48A and the movable ring rail 48B. The movable floor 39 is a surrounding member that is formed by flexibly coupling the many footboards 40, the one X-ray transmission plate 42A, and the one X-ray transmission plate 42B. The X-ray transmission plate 42A and the X-ray transmission plate 42B are disposed between the adjacent footboards within the movable floor 39. X-rays are not transmitted through each footboard 40 and are transmitted through the X-ray transmission plates 42A, 42B. As illustrated in FIG. 5, the width of each footboard 40 in the circumferential direction of the rotary gantry 31 is $W_1$, and each footboard 40 is elongated rectangular in shape and extended in the axial direction of the rotary gantry 31. As illustrated in FIG. 6, the width of each X-ray transmission plate 42A, 42B in the circumferential direction of the rotary gantry 31 is $W_2$, and each X-ray transmission plate 42A, 42B is elongated rectangular in shape and extended in the axial direction of the rotary gantry 31. The width $W_2$ of each X-ray transmission plate 42A, 42B is greater than the width $W_1$ of each footboard 40. The X-ray transmission plates 42A, 42B each include a metal plate 44B, which is formed, for example, of aluminum alloy, and an X-ray transmission portion (X-ray transmission area) 44 through which X-rays are transmitted. The X-ray transmission portion 44 is, for example, a rectangular graphite plate. The width $W_3$ in the circumferential direction of the rotary gantry 31 of the X-ray transmission portion 44 is greater than the width $W_1$ of each footboard 40 and smaller than the width $W_2$ of each X-ray transmission plate 42A, 42B. The movable floor 39 includes footboard groups 41A, 41B, 41C. The X-ray transmission plate 42A is disposed between the footboard group 41A and the footboard group 41C. The X-ray transmission plate 42B is disposed between the footboard group 41B and the footboard group 41C. The X-ray transmission portion 44 is fitted into an opening that is formed in the metal plate 44B and is of the same size as the X-ray transmission portion 44, and is attached integrally to the metal plate 44B. The X-ray transmission portion 44 is surrounded by the metal plate 44B. The X-ray transmission portion 44 may be formed of reinforced glass, plastic, or other X-ray permeable nonmetallic member instead of graphite. The X-ray transmission plates 42A, 42B may be formed of an X-ray permeable nonmetallic member (graphite, reinforced glass, or plastic) without providing the X-ray transmission plates 42A, 42B with the X-ray transmission portion 44.

As for the footboard groups 41A, 41B, 41C, a pair of wheels 45 (see FIG. 18) is rotatably attached to opposite longitudinal ends of each footboard 40. Similarly, the pair of wheels 45 is rotatably attached to the ends of the X-ray transmission plates 42A, 42B. As regards a pair of footboard groups 41A, 41B, 41C, neighboring footboards 40 are flexibly coupled at opposite longitudinal ends of the footboards 40 (the wheels 45 of the neighboring footboards 40 are coupled with a link), and opposite widthwise ends of each footboard are bent inward (refer to Paragraph 0018 and FIG. 4 in Japanese Patent Application Laid-Open No. Hei 11 (1999)-47287). Similarly, the X-ray transmission plate 42A is flexibly coupled to neighboring footboards 40 in the footboard group 41A and to neighboring footboards 40 in the footboard group 41C. Likewise, the X-ray transmission plate 42B is flexibly coupled to neighboring footboards 40 in the footboard group 41B and to neighboring footboards 40 in the footboard group 41C. An end 47B of the movable floor 39 that is positioned toward the rear ring 34, or more specifically, the end 47B of each footboard 40 and of the X-ray transmission plates 42A, 42B that is positioned toward the rear ring 34, moves within the semicylindrical track 102 formed by the movable ring rail 48B. An end 47A of the movable floor 39 that is positioned toward the front ring 33, or more specifically, the end 47A of each footboard 40 and of the X-ray transmission plates 42A, 42B that is positioned toward the front ring 34, moves within the semicylindrical track 102 formed by the stationary ring rail 48A.

Figure 2:
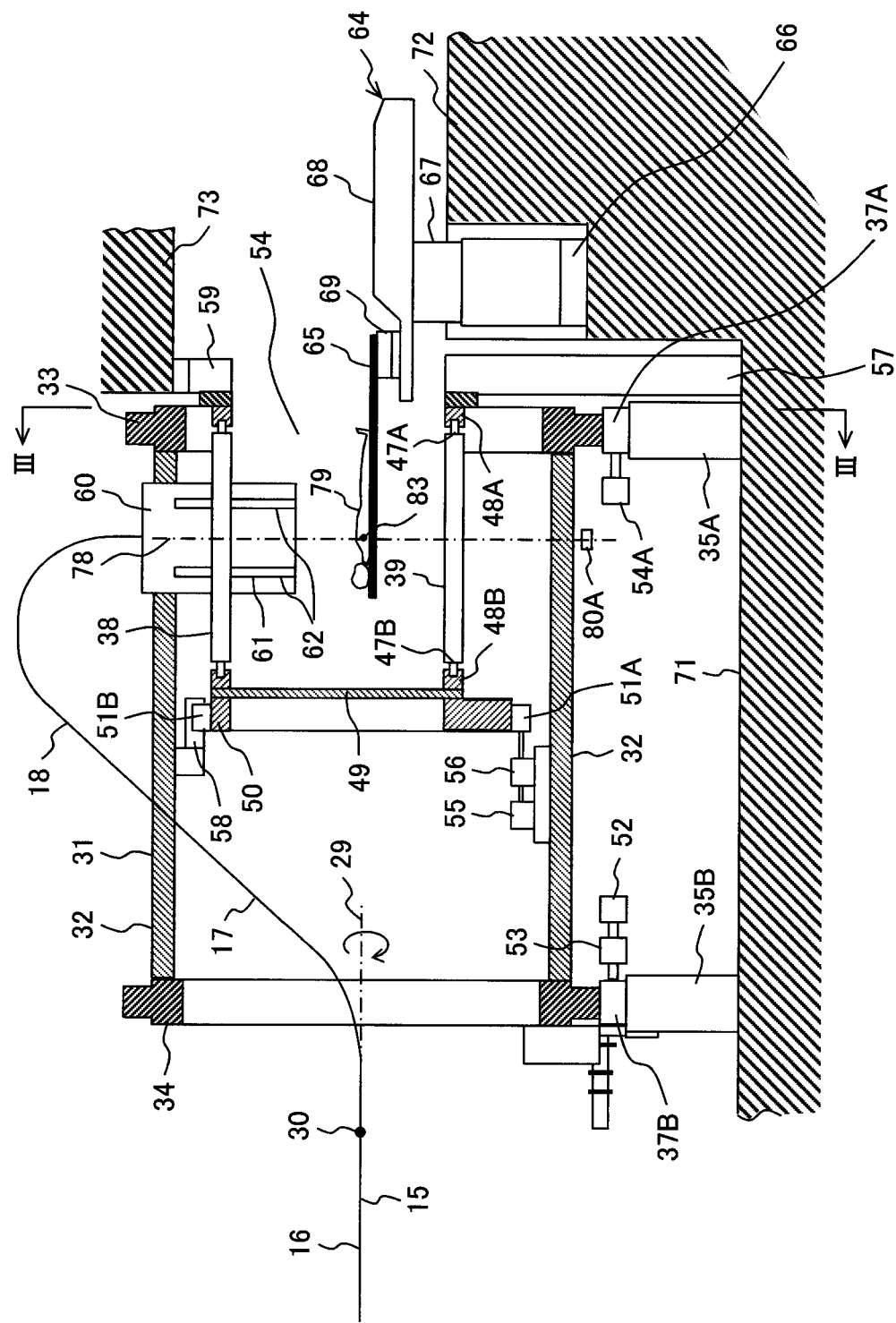
FIG. 2 is an enlarged longitudinal cross-sectional view of a rotary gantry shown in FIG. 1.

As illustrated in FIG. 2, the stationary ring rail 48A is supported by a building ceiling 73 through a fixed support 59 and further supported by the floor 71 through a fixed support 57. The movable ring rail 48B is attached to a rotary ring 50 through the rear panel 49. The rotary ring 50 is supported by the inner surface of the rotary drum 32 of the rotary gantry 31 through multiple support rollers 51B that are disposed along the circumferential direction of the rotary drum 32 and in contact with the outer surface of the rotary ring 50. A ring rail drive device 55, which rotates the movable ring rail 48B in a direction opposite to the direction of rotation of the rotary gantry 31, is connected to a support roller 51A through a speed reduction device 56. The support roller 51A is one of the support rollers 51B. The ring rail drive device 55 and the speed reduction device 56 are mounted on the inner surface of the rotary drum 32.

When the rotary gantry 31 rotates in forward direction, the irradiation device 60 also rotates in forward direction, but the support roller 51A is driven by the ring rail drive device 55 to rotate the movable ring rail 48B in reverse direction. When the rotary gantry 31 rotates in reverse direction, the ring rail drive device 55 rotationally drives the support roller 51A to rotate the movable ring rail 48B in forward direction. As the movable ring rail 48B rotates in a direction opposite to the direction of rotation of the rotary gantry 31, the movable ring rail 48B looks as if it is stopped when viewed from a treatment room 54. As a result, even when the rotary gantry 31 rotates, the therapy cage 38 maintains the semi-cylindrical track 102 (formed of the upper arc portion and the lower horizontal portion). That is to say, the movable floor 39 of the therapy cage 38 constantly forms a horizontal floor portion 46 (see FIGS. 3 and 4) without regard to the rotation angle of the rotary gantry 31.

The movable floor 39 has sufficient rigidity, remains undeformed when the medical technologist 105 works on the movable floor 39, and forms a workspace around the treatment table 64.

In the footboard group 41C, a cover take-up device 43 (see FIG. 4) is disposed between a pair of neighboring footboards 40. In coordination with the generation of an opening 104 between the pair of neighboring footboards 40, the cover take-up device 43 takes up a cover 42 so as to cover the opening 104 (see the later-mentioned FIG. 11). The cover take-up device 43 may be structured by using a publicly known technology such as a roll screen or roll curtain structured to maintain tension applied to a take-up pipe.

A connection member 61 between opposite ends (footboard groups 41A, 41B) of the movable floor 39 and the irradiation device 60 will now be described with reference to FIG. 4. The connection member 61 includes a pair of slide members 63A, 63B and a pair of guide rails 62. The connection member 61 is disposed on each of a pair of lateral surfaces of the irradiation device 60 that oppose each other in the rotation direction of the rotary gantry 31. The pair of slide members 63A, 63B is respectively mounted on one end of the footboard groups 41A, 41B. The pair of guide rails 62, which are guide members, are respectively mounted on a pair of lateral surfaces of the irradiation device 60, which oppose each other in the rotation direction of the rotary gantry 31. The slide members 63A, 63B mounted on one end of the footboard group 41A are movably mounted separately on the pair of guide rails 62 disposed on a lateral surface of the irradiation device 60. The slide members 63A, 63B mounted on one end of the footboard group 41B are movably mounted separately on the pair of guide rails 62 disposed on the other lateral surface of the irradiation device 60. As a result, one end each of the footboard groups 41A, 41B is connected slidably in the radial direction of the rotary gantry 31 to each of the pair of lateral surfaces of the irradiation device 60 by the connection member 61 (the slide members 63A, 63B and the pair of guide rails 62).

The irradiation device 60 is tapered toward the rotation center of the rotary gantry 31. Consequently, the pair of lateral surfaces of the irradiation device 60, which oppose each other in the rotation direction of the rotary gantry 31, are each inclined with respect to the rotation plane normal to the rotary gantry 31.

The treatment room 54 is shaped such that it is surrounded by the movable floor 39 of the therapy cage 38 in the rotary drum 32. The treatment room 54 is open toward the front ring 33 and closed by the rear panel 49, which is disposed toward the rear ring 34 of the treatment room 54. The irradiation device 60 is mounted on the rotary drum 32, and extended toward the center of the rotary drum 32 until it reaches the inside of the treatment room 54, which is formed inward from the movable floor 39. The beam path 18 of the GABT system 17, which is connected to the irradiation device 60, is extended toward the rear ring 34 to communicate with the beam path 16 of the HEBT system 15 at the interface 30 positioned outside of the rotary gantry 31 as illustrated in FIG. 2. The central axis 29 (see FIGS. 1 and 2) of the rotary gantry 31, which is the rotation center of the rotary gantry 31, passes through the center of the entrance of the beam path 18 at the interface 30.

Figure 7:
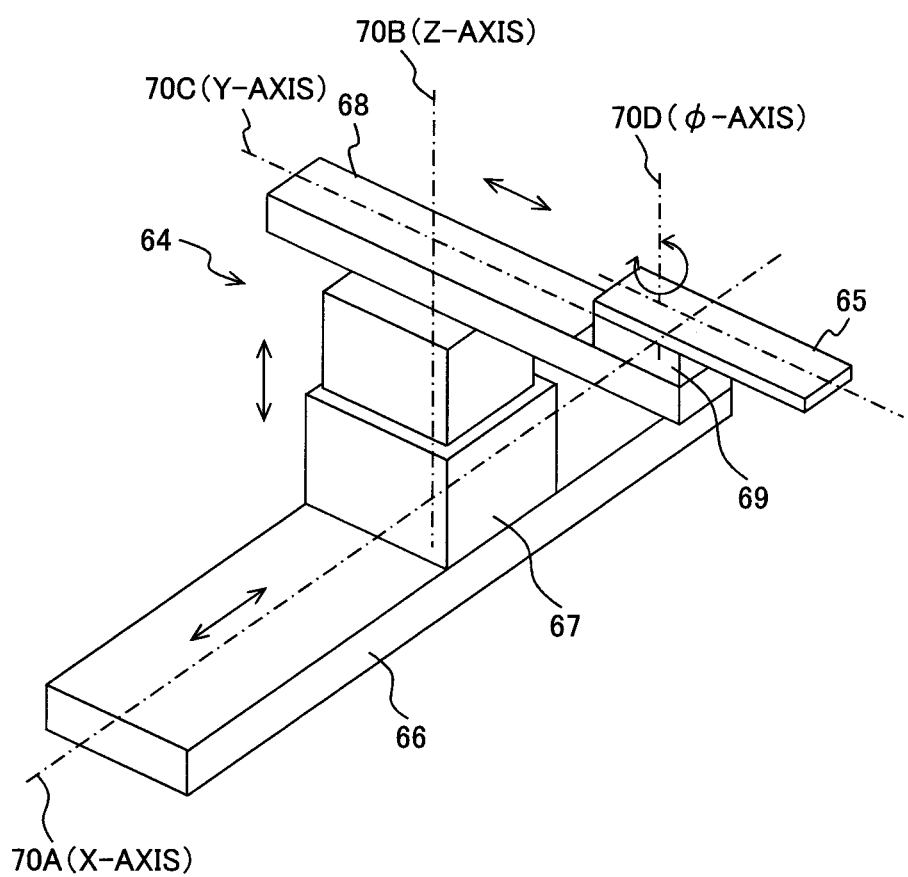
FIG. 7 is a perspective view of a treatment table shown in FIG. 2.

As illustrated in FIGS. 2 and 7, the treatment table 64 includes a bed 65, an X-direction drive mechanism 66, a Y-direction drive mechanism 68, an up-down direction drive mechanism 67, and a rotary drive mechanism 69. These drive mechanisms are disposed outside of the rotary drum 32. The X-direction drive mechanism 66, which moves the bed 65 in a direction orthogonal to the rotation axis of the rotary gantry 31, is disposed in a treatment table mounting area 72, which is positioned above the floor 71. The up-down direction drive mechanism 67 is disposed over the X-direction drive mechanism 66. The Y-direction drive mechanism 68 is disposed over the up-down direction drive mechanism 67. The rotary drive mechanism 69 is disposed over the Y-direction drive mechanism 68. The bed 65 is disposed over the rotary drive mechanism 69 and supported by each drive mechanism. The Y-direction drive mechanism 68 moves the bed 65 in a direction in which the rotation axis of the rotary gantry 31 is extended. The rotary drive mechanism 69 rotates the bed 65 in a horizontal plane.

The treatment room 54 is formed relative to the space in the rotary drum 32 of the rotary gantry 31 that is partitioned by the rear panel 49. The treatment room 54 is set at a floor level near the rotation center that provides the rotation radius of the rotary gantry 31. Thus, the treatment room 54 is usually positioned 6 to 8 m above the lowest position of the inner surface of the rotary drum 32. Therefore, the patient 79 on the bed 65 of the treatment table 64 is positioned in a space having the above-mentioned height. Consequently, the therapy cage 38, which creates a space around the patient 79, is required to provide a safe place for patients and medical technologists.

The particle beam therapy system 1 includes a radiographic imaging apparatus in order to acquire image information about a diseased part, which is used to position a patient before particle beam irradiation onto the patient and confirm the position of the patient during particle beam irradiation. The radiographic imaging apparatus includes X-ray sources (X-ray generation devices) 80A, 80B, flat-panel detectors (FPDs) 82A, 82B, which act as a radiation detection device, collimators 81A, 81B, signal processing devices 93 (FIG. 8), an imaging processing device 94 (FIG. 8), and an input device 101. The radiographic imaging apparatus further includes a rotating body (rotary gantry 31) to which the X-ray sources 80A, 80B, the FPDs 82A, 82B, and the collimators 81A, 81B are attached. The rotating body rotates around the bed 65.

In the particle beam therapy system 1, the X-ray sources 80A, 80B are positioned at the central axis 78 of the irradiation device 60 in the axial direction of the rotary gantry 31 (see FIG. 2). An FPD is a planar thin radiation detection device. Two types of FPDs are available: a direct conversion FPD and an indirect conversion FPD.

The direct conversion FPD is formed by arranging many semiconductor radiation detectors in a two-dimensional matrix form. In the direct conversion FPD, each of the semiconductor radiation detectors arranged in a matrix form is a radiation detection element.

The indirect conversion FPD includes a scintillator and many semiconductor elements (e.g., photodiodes). The scintillator is disposed on the front surface to permit the incidence of X-rays. The many semiconductor elements are arranged in a two-dimensional matrix form, attached to the rear surface of the scintillator, and used to perform photoelectric conversion. The scintillator covers the whole surface of the many semiconductor elements. In the indirect conversion FPD, one radiation detection element is substantially formed by one semiconductor element and a micro area of the scintillator. The micro area of the scintillator is positioned in front of the one semiconductor element to generate light that is to be inputted to the semiconductor element. Therefore, it can be said that the indirect conversion FPD is formed by arranging many radiation detection elements in a two-dimensional matrix form.

Figure 11:
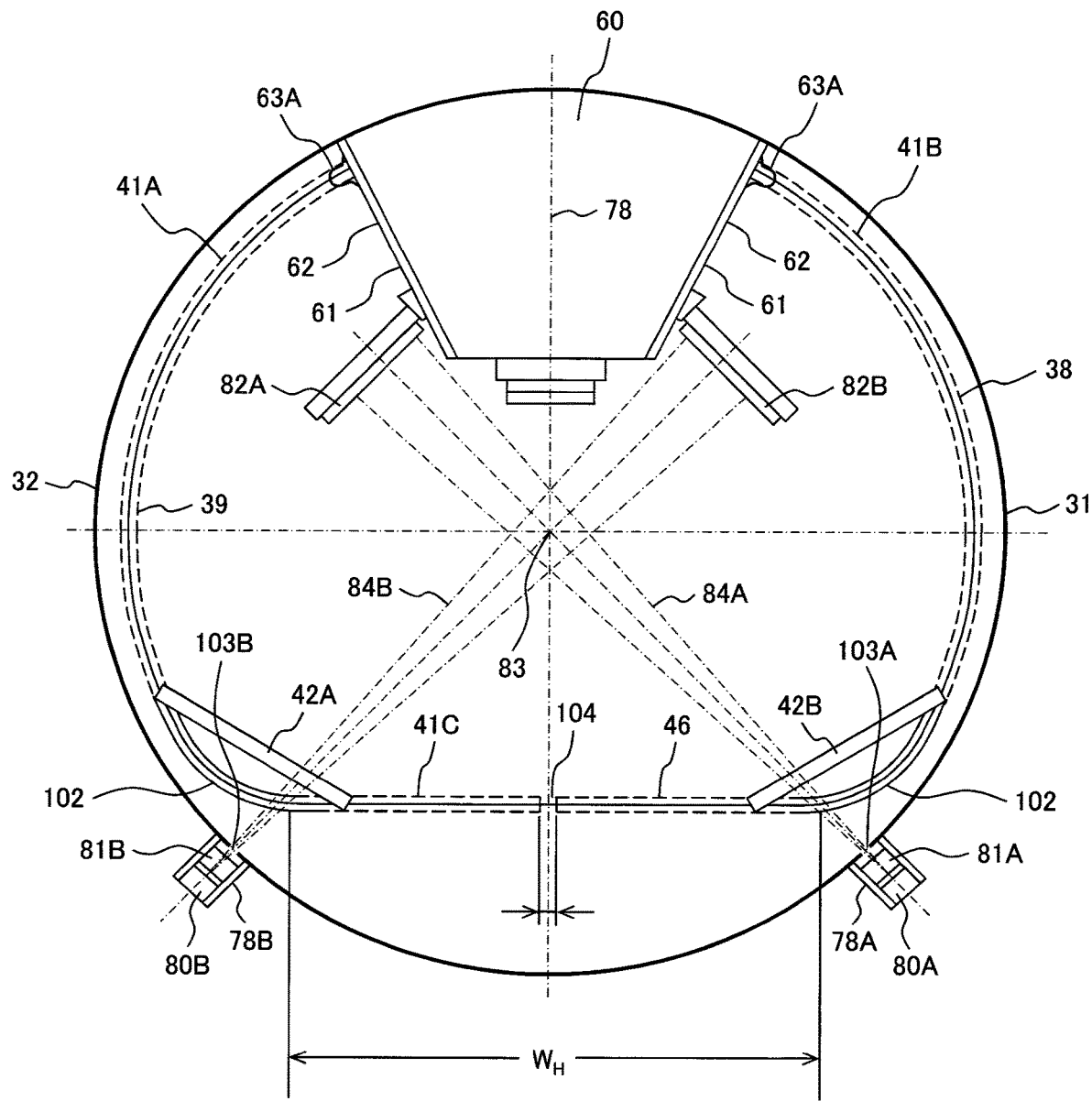
FIG. 11 is a diagram illustrating the status of a movable floor of the radiotherapy cage when the rotation angle of the rotary gantry shown in FIGS. 2 and 3 is 0 degrees.

As illustrated in FIG. 11, the X-ray source 80A is disposed outside the rotary drum 32 of the rotary gantry 31 and attached to the outer surface of the rotary drum 32 by a support member 78A. The collimator 81A is positioned in front of the X-ray source 80A, disposed outside the rotary drum 32, and attached to the support member 78A. The FPD 82A is disposed to face the X-ray source 80A so that X-rays 84A emitted from the X-ray source 80A are incident on the FPD 82A, is positioned within the treatment room 54, and is attached to one lateral surface of the irradiation device 60 in its rotation direction. A through hole (X-ray passage hole) 103A is formed in the rotary drum 32. The through hole 103A is positioned to face the X-ray source 80A, and is sized to permit the passage of X-rays emitted from the X-ray source 80A. Further, the X-ray source 80A and the through hole 103A face the X-ray transmission plate 42B included in the movable floor 39.

The X-ray source 80B is disposed outside the rotary drum 32 of the rotary gantry 31. As illustrated in FIG. 11, the X-ray source 80B is mounted on the outer surface of the rotary drum 32 by the support member 78A. The collimator 81B is positioned in front of the X-ray source 80B, disposed outside of the rotary drum 32, and attached to a support member 78B. The FPD 82B is disposed to face the X-ray source 80B so that X-rays 84B emitted from the X-ray source 80B are incident on the FPD 82B, is positioned within the treatment room 54, and is attached to the other lateral surface of the irradiation device 60 in its rotation direction. A through hole (X-ray passage hole) 103B is formed in the rotary drum 32. The through hole 103B is positioned to face the X-ray source 80B, and is sized to permit the passage of X-rays emitted from the X-ray source 80B. Further, the X-ray source 80B and the through hole 103B face the X-ray transmission plate 42A included in the movable floor 39. The X-ray transmission portion 44 of the X-ray transmission plate 42A is disposed to face the X-ray source 80B. The X-ray transmission portion 44 of the X-ray transmission plate 42B is disposed to face the X-ray source 80A.

As regards the FPDs 82A, 82B, their planes (e.g., an approximately 43-cm square) respectively facing, for example, the X-ray transmission plates 42A, 42B are such that, for example, an X-ray incident surface is substantially formed by arranging radiation detection elements (not shown), which are approximately 0.14-mm squares, in 3072 columns and 3072 rows.

An angle of 90 degrees is formed between a straight line connecting an isocenter 83 to a hole (not shown) formed in the collimator 81A through which X-rays pass and a straight line connecting the isocenter 83 to a hole (not shown) formed in the collimator 81B through which X-rays pass (see FIG. 11). Therefore, the X-ray source 80A and the X-ray source 80B differ in angular position by 90 degrees in the circumferential direction of the rotary gantry 31. The isocenter 83 is a point of intersection between the central axis 78 of the irradiation device 60 and the rotation axis 29, which is the center of rotation of the rotary gantry 31.

Figure 13A:
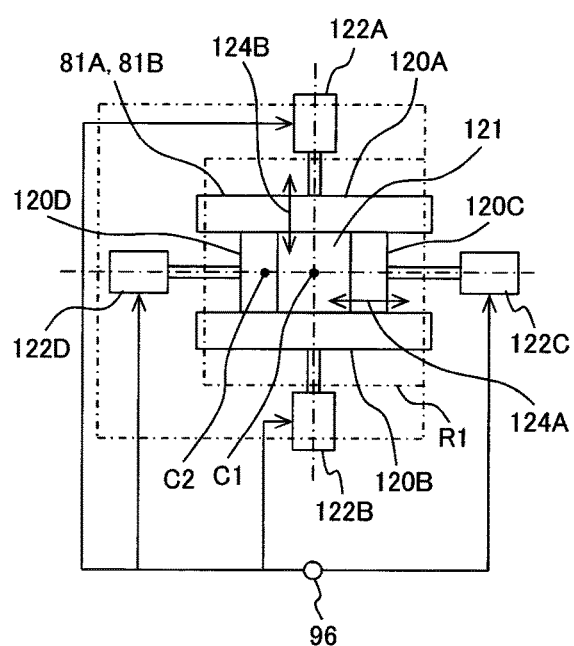
FIG. 13A is a diagram illustrating a detailed configuration of a collimator and a view taken along line XIIIA-XIIIA of FIG. 12A showing an aperture of the collimator with respect to a small FOV.
Figure 13B:
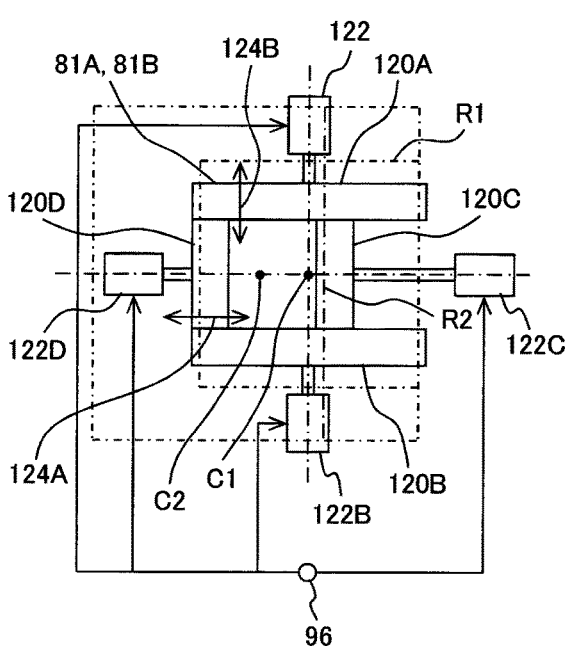
FIG. 13B is a diagram illustrating a detailed configuration of a collimator and a view taken along line XIIIB-XIIIB of FIG. 12B showing an aperture of the collimator with respect to a large FOV.

As illustrated in FIGS. 13A and 13B, the collimator 81B includes diaphragm members 120A, 120B, 120C, 120D, which are formed of a radiation shielding material. The diaphragm members 120A, 120B are disposed to face each other in the axial direction of the rotary gantry 31. The diaphragm members 120A, 120B are disposed between a pair of guide members (not shown) that is disposed in parallel with the diaphragm members 120C, 120D. Opposite ends of each of the diaphragm members 120A, 120B are movably attached to the pair of guide members. The diaphragm members 120C, 120D are disposed in a direction orthogonal to the diaphragm members 120A, 120B (in the circumferential direction of the rotary gantry 31). Opposite ends of each of the diaphragm members 120C, 120D are movably attached to another pair of guide members (not shown) that is disposed in parallel with the diaphragm members 120A, 120B. The collimator 81B is disposed in front of the X-ray source 80B so that the diaphragm member 120C is positioned toward the irradiation device 60 rather than the collimator 81A.

As is the case with the collimator 81B, the collimator 81A is structured as illustrated in FIGS. 13A and 13B. However, the collimator 81A is disposed in front of the X-ray source 80A so that the diaphragm member 120C is positioned toward the irradiation device 60 rather than the collimator 81B.

In each of the collimators 81A, 81B, an aperture 121 through which X-rays pass is formed as it is surrounded by the diaphragm members 120A, 120B, 120C, 120D. A transport device 122A is coupled to the diaphragm member 120A, a transport device 122B is coupled to the diaphragm member 120B, a transport device 122C is coupled to the diaphragm member 120C, and a transport device 122D is coupled to the diaphragm member 120D. The diaphragm members 120A, 120B are moved by the transport devices 122A, 122B in the direction of arrow 124B (the Y-axis direction shown in FIG. 16, that is, the central axis direction of the rotary gantry 31), and the diaphragm members 120C, 120D are moved by the transport devices 122C, 122D in the direction of arrow 124A (the X-axis direction shown in FIG. 16, that is, the circumferential direction of the rotary gantry 31). The position and size of the aperture 121 can be changed by moving the diaphragm members 120A, 120B, 120C, 120D.

Figure 8:
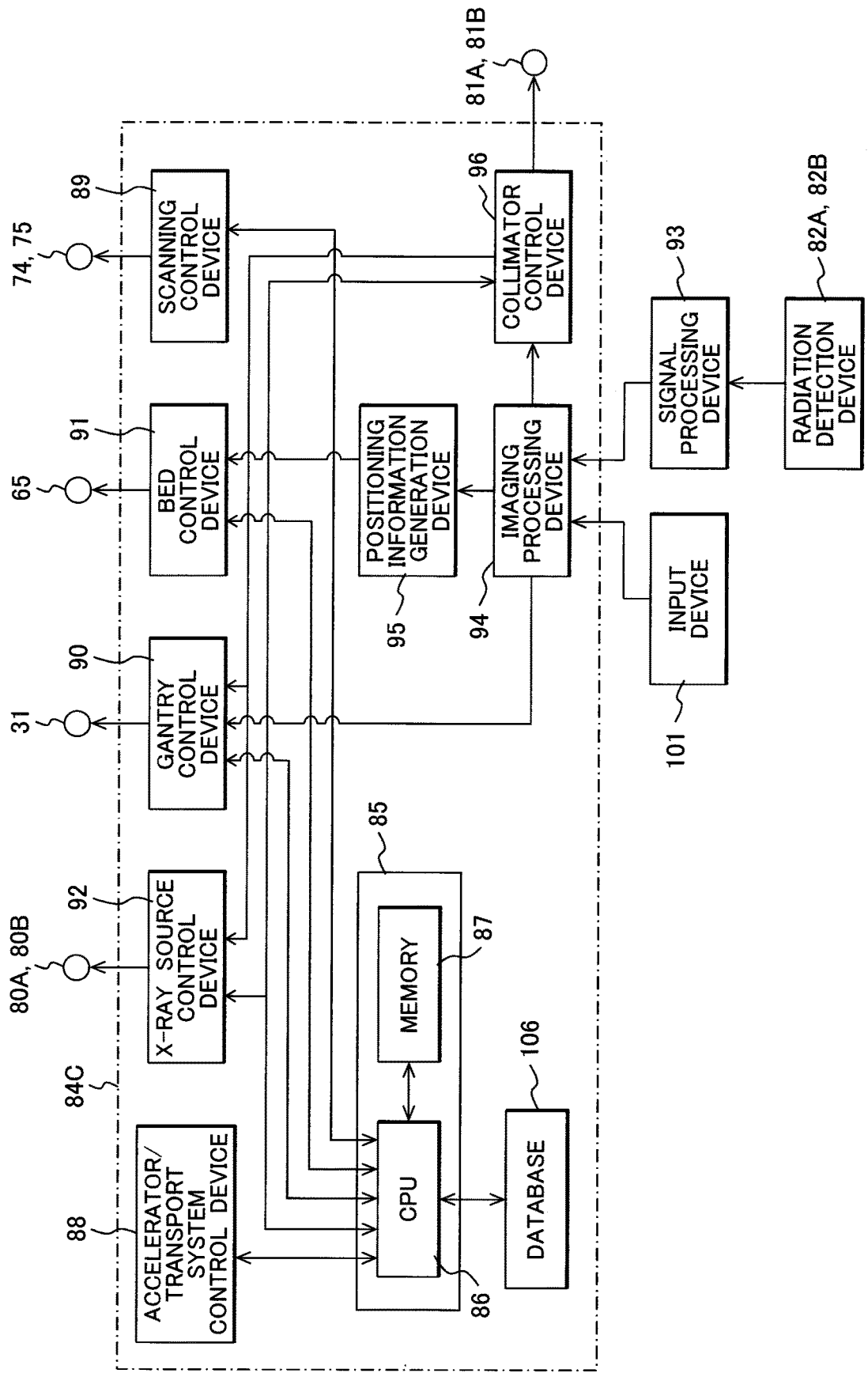
FIG. 8 is a diagram illustrating a detailed configuration of a control system shown in FIG. 1.
Figure 9:
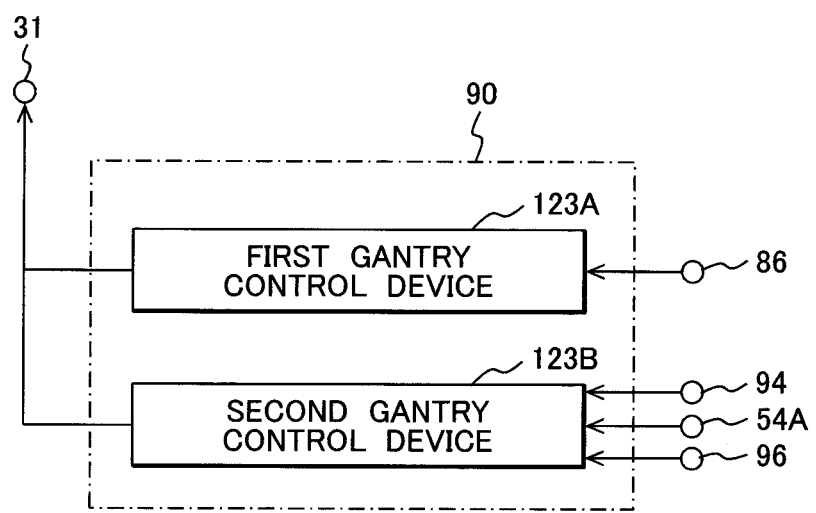
FIG. 9 is a diagram illustrating a detailed configuration of a gantry control device shown in FIG. 8.

As illustrated in detail in FIG. 8, the control system 84C includes a central control device 85, an accelerator/transport system control device 88, a scanning control device 89, a gantry control device 90, a bed control device 91, X-ray source control device 92, an imaging processing device 94, a positioning information generation device 95, a collimator control device 96, and a database 106. The central control device 85 includes a central processing unit (CPU) 86 and a memory 87 connected to the CPU 86. The CPU 86 is connected to the accelerator/transport system control device 88, the scanning control device 89, the bed control device 91, the X-ray source control device 92, the imaging processing device 94, the positioning information generation device 95, and the collimator control device 96. The X-ray source control device 92 is connected to the collimator control device 96. As illustrated in FIG. 9, the gantry control device 90 includes a first gantry control device 123A and a second gantry control device 123B. The first gantry control device 123A is connected to the CPU 86, and the second gantry control device 123B is connected to the later-described imaging processing device 94 and to the collimator control device 96. The positioning information generation device 95 is connected to the bed control device 91. The database 106 is connected to the CPU 86. The particle beam therapy system 1 includes a therapy planning device 107. The therapy planning device 107 is connected to the database 106.

Figure 10:
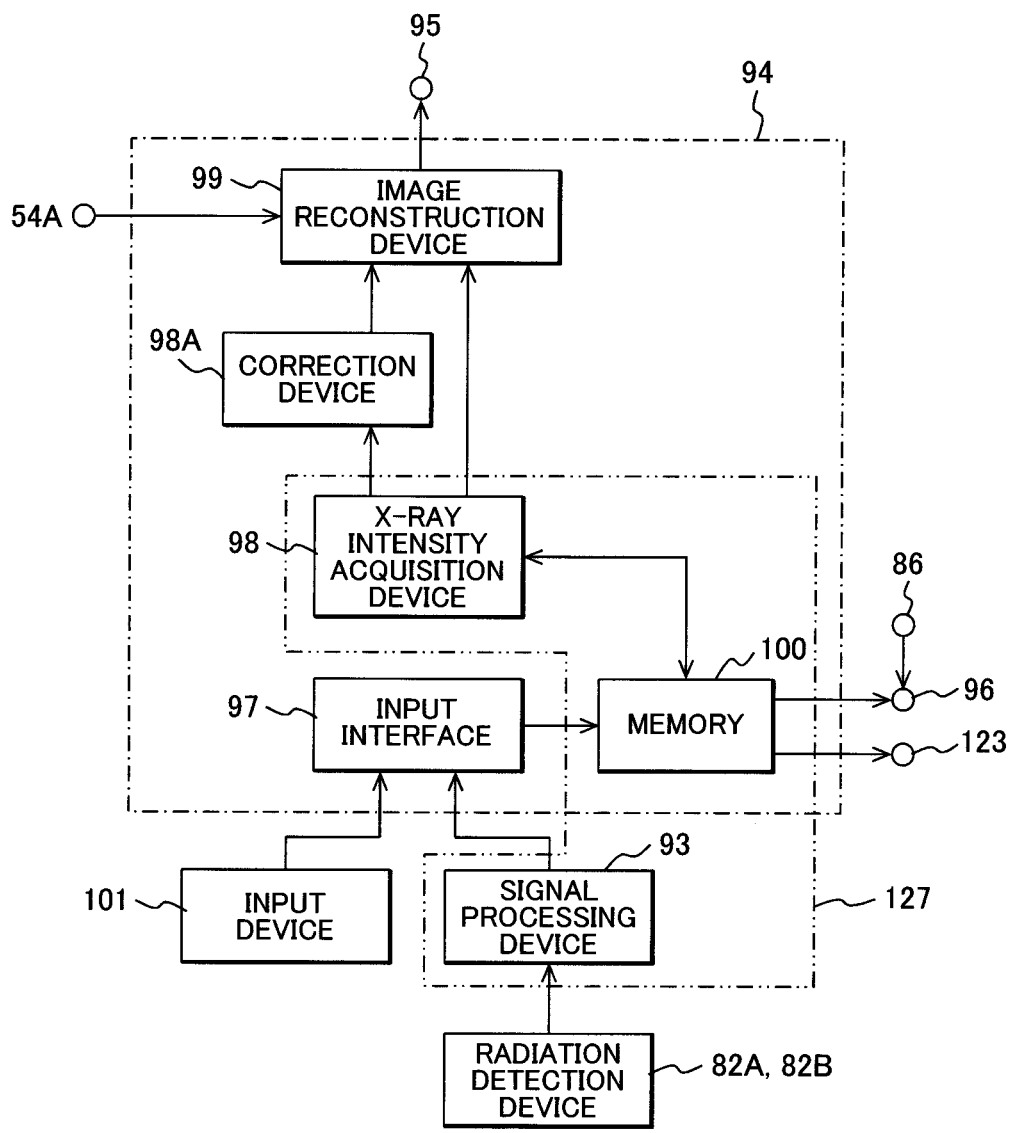
FIG. 10 is a diagram illustrating a detailed configuration of an imaging processing device shown in FIG. 8.

As illustrated in FIG. 10, the imaging processing device 94 includes an input interface 97, an X-ray intensity acquisition device 98, a correction device 98A, an image reconstruction device (tomographic information generation device) 99, and a memory 100. The memory 100 is connected to the input interface 97 and to the X-ray intensity acquisition device 98. The correction device 98A is connected to the X-ray intensity acquisition device 98, and the image reconstruction device 99 is connected to the correction device 98A. The input device 101 and two signal processing devices 93 are connected to the input interface 97. Many radiation detection elements (not shown) of the FPD 82A, or more specifically, photodiodes, are connected to one signal processing device 93, and many radiation detection elements (not shown) of the FPD 82B, or more specifically, photodiodes, are connected to the other signal processing device 93. The memory 100 is connected to the gantry control device 90 and to the collimator control device 96. The image reconstruction device 99 is connected to the positioning information generation device 95.

Before an ion beam emitted from the synchrotron accelerator 3 is irradiated onto a diseased part of the patient 79, the radiographic imaging apparatus is used to radiograph the patient 79. Two radiographic imaging modes are selectable for the patient 79: a first imaging mode and a second imaging mode. The first imaging mode is for the head and neck of the patient 79, that is, a first radiation target. The second imaging mode is for the trunk of the patient 79, that is, a second radiation target. The second radiation target is greater than the first radiation target. The first radiation target includes the head and the neck. The first imaging mode includes a head imaging mode and a neck imaging mode.

Figure 3:
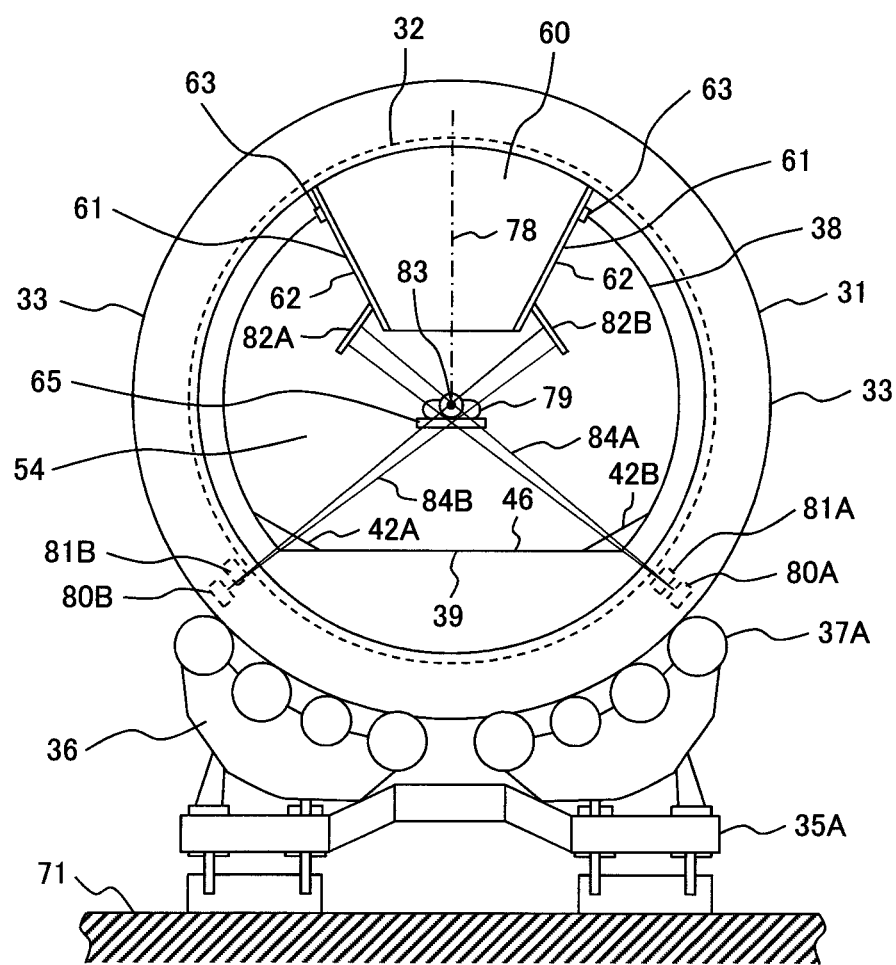
FIG. 3 is a cross-sectional view taken along line III-III of FIG. 2.

Before irradiating a diseased part with an ion beam, the present embodiment performs diseased part positioning to align the diseased part with the central axis 78 of the irradiation device 60 (see FIGS. 2 and 3). In order to achieve diseased part positioning, X-ray CT imaging is performed on the vicinity of the diseased part of the patient 79 lying on the bed 65 (hereinafter referred to as current X-ray CT imaging) to generate three-dimensional image information about the vicinity of the diseased part. Current X-ray CT imaging performed by using the X-ray sources 80A, 80B and the FPDs 82A, 82B is described below.

Figure 12A:
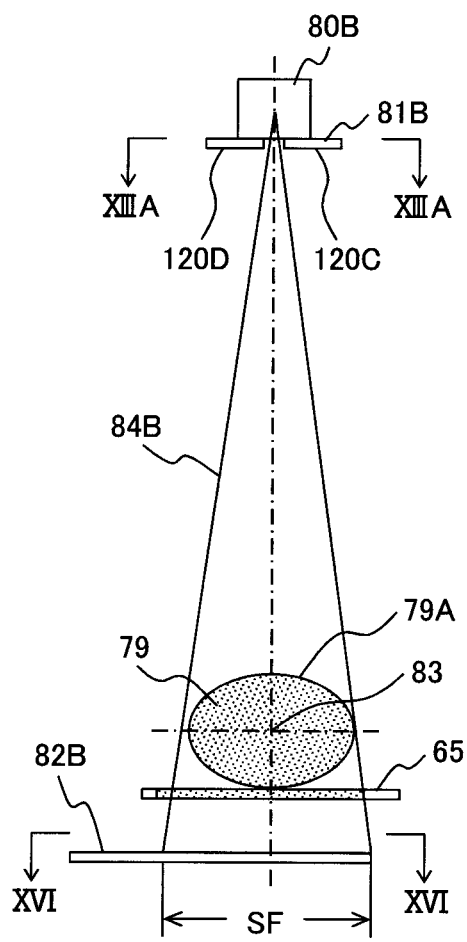
FIG. 12A is a diagram illustrating how X-rays are emitted from an X-ray source to a radiation target (small FOV) and how X-rays transmitted through the radiation target (small FOV) are detected.

It is assumed that the diseased part to be irradiated with an ion beam is a brain tumor in the head 79A of the patient 79 (see FIG. 12A). In the current X-ray CT imaging, X-ray imaging is performed on the head 79A in the first imaging mode. Before the head 79A of the patient is irradiated with X-rays, the bed 65 is moved by using a pendant (not shown) in a manner described in Japanese Patent Application Laid-Open No. 2006-239403 as needed to position the diseased part of the head 79A of the patient 79 lying on the bed 65. More specifically, positioning information inputted from the pendant by an operator is inputted to the bed control device 91 in order to let the bed control device 91 exercise control to drive the X-direction drive mechanism 66, the Y-direction drive mechanism 68, the up-down direction drive mechanism 67, and the rotary drive mechanism 69. This moves the bed 65 as needed to roughly position the diseased part of the head 79A with respect to the central axis 78 of the irradiation device 60. The X-direction drive mechanism 66 moves along an X-axis 70A parallel to the front ring 33, and the up-down direction drive mechanism 67 moves in an up-down direction along a Z-axis 70B perpendicular to the X-axis 70A. The Y-direction drive mechanism 68 moves along a Y-axis 70C orthogonal to the X-axis in a horizontal direction. The rotary drive mechanism 69 rotates the bed 65 around a φ-axis 70D parallel to the Z-axis 70B. One or more of the above drive mechanisms are used as needed to achieve the above-described diseased part positioning. In the above instance, the rotation angle of the rotary gantry 31 is, for example, 0 degrees so that the central axis 78 of the irradiation device 60 is perpendicular to the floor 71 of the building.

A different operator enters, into the input device 101, a radiation target, that is, "head", and a dimension of the head 79A of the patient 79 in the width direction of the bed 65 (the width of the head). The radiation target, that is, "head", and the information about the width of the head 79A serve as small FOV information (first imaging mode information). The small FOV information, which is the inputted FOV information (imaging mode information), is stored in the memory 100 through the input interface 97. The input device 101, which inputs the imaging mode information (first imaging mode information and second imaging mode information (large FOV information)), functions as an imaging mode designation device. In the first imaging mode, which is used for "neck", "neck" and a dimension of the neck of the patient 79 in the width direction of the bed 65 (the width of the neck) are inputted from the input device 101 as the small FOV information, which is the first imaging mode information.

After the diseased part of the head 79A is positioned, the different operator enters an "X-ray irradiation start command" into the input device 101. The X-ray irradiation start command is then inputted from the input device 101 to the X-ray source control device 92 and to the collimator control device 96. Upon receipt of the X-ray irradiation start command, the collimator control device 96 exercises control to drive the transport devices 122A, 122B, 122C, 122D of the collimators 81A, 81B. The diaphragm members 120A, 120B, 120C, 120D are then moved to adjust the size of the aperture 121. In this instance, the size of the aperture 121 is adjusted so that the X-rays are irradiated onto the head 79A, transmitted through the head 79A, and incident on a small FOV area (first field-of-view area (first FOV area)) R1 (see FIG. 16) of each of the FPDs 82A, 82B. The small FOV area R1 is the area of a square abcd shown in FIG. 16. The center of the aperture 121 of the small FOV area R1 coincides with the isocenter 83.

Figure 16:
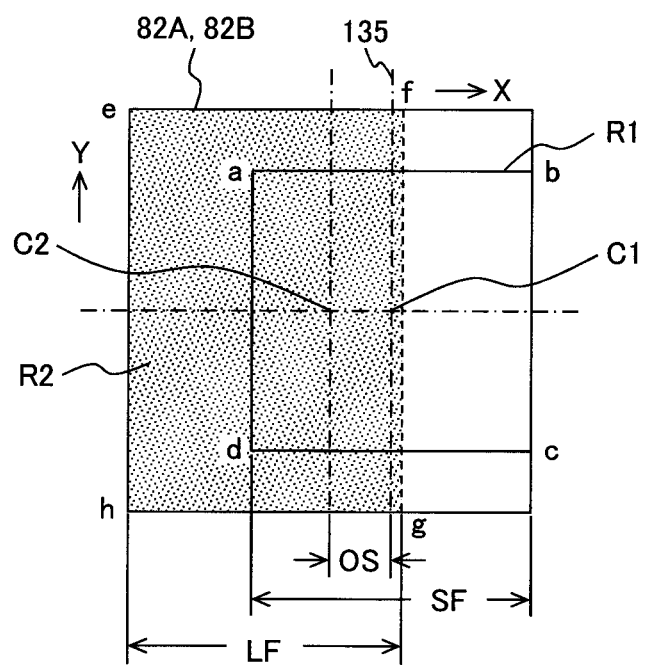
FIG. 16 is a diagram illustrating an X-ray detection area of an FPD shown in FIG. 11 for a small FOV and for a large FOV.

The length of one side of the small FOV area R1 of the square shown in FIG. 16 is SF. The center C1 (first center) of the small FOV area R1 of the FPD 82B is on the extension of a straight line (first straight line) connecting the X-ray generation point of the X-ray source 80B to the isocenter 83 (the point of intersection between the central axis 78 and the rotation axis 29). The center C1 of the small FOV area R1 is deviated by an offset amount OS from a center C2 (second center) of the FPD 82B (or the FPD 82A) in the direction of extension of a one-dot chain line connecting the center C1 to the center C2. The center C1 of the small FOV area R1 of the FPD 82A is on the extension of a straight line connecting the X-ray generation point of the X-ray source 80A to the isocenter 83. Referring to FIG. 16, R2 is a large FOV area of each of the FPDs 82A, 82B, and C2 is the center of each of the FPDs 82A, 82B. The large FOV area R2 is the area of a rectangle efgh shown in FIG. 16. The length of the large FOV area R2 in the circumferential direction of the rotary gantry 31 is LF.

The small FOV area R1 of the square abcd of each of the FPDs 82A, 82B is an area where multiple radiation detection elements for detecting X-rays in the first imaging mode are disposed, and is left-right symmetrical with respect to a straight one-dot chain line 135 (second straight line) that is passed through the center C1 and extended in the direction of the rotation axis 29 of the rotary gantry 31 (is symmetrical in the circumferential direction of the rotary gantry 31). That is to say, the center C1 of each of the FPDs 82A, 82B is a point of intersection between each of the FPDs 82A, 82B and a straight line passing from the associated x-ray source to the rotation center (rotation axis 29) of the rotary gantry 31. The FPD 82B is attached to the other lateral surface of the irradiation device 60 so that the center C1 of the small FOV area R1 is positioned toward the irradiation device 60 rather than the center C2 of the FPD 82B. The FPD 82A is attached to the one lateral surface of the irradiation device 60 so that the center C1 of the small FOV area R1 is positioned toward the irradiation device 60 rather than the center C2 of the FPD 82A.

The large FOV area R2 of each of the FPDs 82A, 82B, which is the rectangle efgh extended in the direction of the rotation axis 29, is an area where multiple radiation detection elements for detecting X-rays in the second imaging mode are disposed, and is not left-right symmetrical with respect to the one-dot chain line 135 (is not symmetrical in the circumferential direction of the rotary gantry 31). In the circumferential direction of the rotary gantry 31, an edge (the side fg of the rectangle efgh) of the large FOV area R2 is positioned toward the irradiation device 60 rather than the center C1.

The FPDs 82A, 82B used in the present embodiment are, for example, indirect conversion FPDs. Position codes assigned to the radiation detection elements included in the FPDs 82A, 82B are represented, for example, by $P_{ij}$. i is an integer between 1 and N and indicative of the column number of a radiation detection element. j is an integer between 1 and M and indicative of the row number of a radiation detection element. In the present embodiment, the FPDs 82A, 82B are each formed by arranging the radiation detection elements in 3072 columns and 3072 rows. Therefore, the maximum values of N and M are both "3072".

Referring to FIG. 16, when the direction of the one-dot chain line connecting the center C1 to the center C2 is the X-direction, and the direction orthogonal to the one-dot chain line is the Y-direction, the position information about the radiation detection elements indicated by the position codes $P_{ij}$ is represented by coordinates $(X_i, Y_j)$. In the subsequent description, $P_{ij}$ $(X_i, Y_j)$ represents the position information $(X_i, Y_j)$ about the radiation detection elements indicated by the position codes $P_{ij}$.

Figure 14:
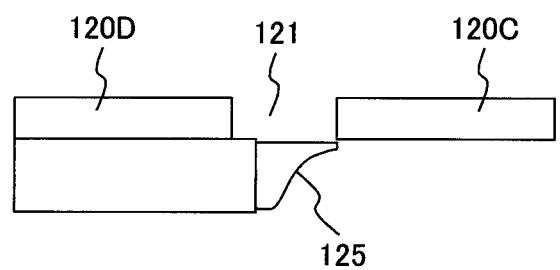
FIG. 14 is a diagram illustrating an X-ray filter mounted on a diaphragm member of the collimator.
Figure 15:
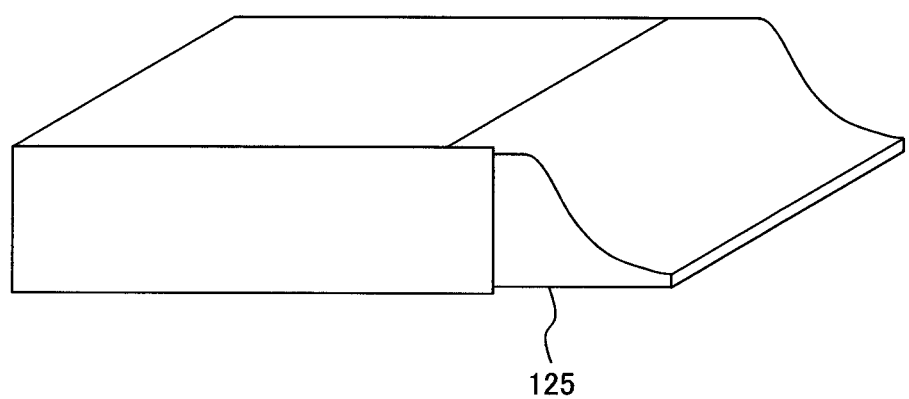
FIG. 15 is an enlarged perspective view of the X-ray filter shown in FIG. 14.

An x-ray filter 125 is attached to a surface of the diaphragm member 120D of the collimator 81A that faces the FPD 82A and to a surface of the diaphragm member 120D of the collimator 81B that faces the FPD 82B (see FIG. 14). The X-ray filter 125 is a bow tie filter having a shape shown in FIG. 15 and a thickness that curvedly decreases toward a tip. In the collimators 81A, 81B, the X-ray filter 125 protrudes from the diaphragm member 120D toward the diaphragm member 120C, and is disposed between the collimator 81A and the outer surface of the rotary drum 32 and between the collimator 81B and the outer surface of the rotary drum 32. The collimator control device 96 drives the transport device 122 to move the diaphragm member 120D toward the diaphragm member 120C so that the X-ray filter 125 soon covers the aperture 121 from the underside of the diaphragm member 120D.

After the diaphragm members 120A-120D of the collimators 81A, 81B are set at predetermined positions based on the small FOV information, the collimator control device 96 outputs diaphragm member setup completion information to the X-ray source control device 92 and to the second gantry control device 123B. Upon receipt of the diaphragm member setup completion information, the X-ray source control device 92, which has already inputted the X-ray irradiation start command, outputs an X-ray irradiation command to the X-ray sources 80A, 80B. This causes the X-ray sources 80A, 80B to emit X-rays. Meanwhile, upon receipt of the diaphragm member setup completion information, the second gantry control device 123B outputs a rotation command to a rotation device 52 of the rotary gantry 31 based on the small FOV information read from the memory 100. The rotation command rotates the rotary gantry 31 within an angular range, for example, of 0 to 200 degrees. The rotation device 52 is driven based on the rotation command to rotate the rotary gantry 31 from 0 to 200 degrees.

As described above, current X-ray CT imaging is performed on the head 79A in the first imaging mode while rotating the rotary gantry 31. FIG. 12A illustrates a state where the X-rays 84B emitted from the X-ray source 80B fall on the head 79A to let the FPD 82B detect the X-rays 84B transmitted through the head 79A. A state where the FPD 82A detects the X-rays 84A emitted from the X-ray source 80A is substantially the same as the state illustrated in FIG. 12A except that the small FOV area R1 having a length of SF and the large FOV area R2 having a length of LF are left-right reversed.

In current X-ray CT imaging, the X-rays 84A, 84B emitted from the X-ray sources 80A, 80B fall on the head 79A of the patient 79 while the rotary gantry 31 is rotating. The X-rays 84A emitted from the X-ray source 80A are passed through the aperture 121 (FIG. 13A), which is set in the collimator 81A, forwarded through the X-ray filter 125 (FIG. 14), passed through the through hole 103A, transmitted through the X-ray transmission portion 44 of the X-ray transmission plate 42B, and irradiated onto the diseased part of the head 79A and onto the vicinity of the diseased part.

The X-rays 84A transmitted through the head 79A are mainly detected by the radiation detection elements in the small FOV area R1 of the FPD 82A (see FIG. 12A). Further, the X-rays 84B emitted from the X-ray source 80B are passed through the aperture 121 (FIG. 13A), which is set in the collimator 81B, forwarded through the X-ray filter 125 (FIG. 14), passed through the through hole 103B, transmitted through the X-ray transmission portion 44 of the X-ray transmission plate 42A, and irradiated onto the diseased part of the head 79A and onto the vicinity of the diseased part. The X-rays 84B transmitted through the head 79A are mainly detected by the radiation detection elements in the small FOV area R1 of the FPD 82B (see FIG. 12A).

The rotary gantry 31 rotates the X-ray sources 80A, 80B around the head 79A. When the rotation angle of the rotary gantry 31, which is measured by the angle detector 54A, is 200 degrees, the second gantry control device 123B, which inputs the rotation angle from the angle detector 54A, outputs a rotation stop command to the rotation device 52. This not only stops the rotation of the rotation device 52, but also stops the rotation of the rotary gantry 31. Upon receipt of the rotation stop command from the second gantry control device 123B, the X-ray source control device 92 outputs an X-ray emission stop command to the X-ray sources 80A, 80B. This stops the X-ray emission from the X-ray sources 80A, 80B so as to stop the X-ray irradiation onto the diseased part of the head 79A.

Each radiation detection element in all the areas of the FPD 82A, which has detected the X-rays 84A, outputs an X-ray detection signal. The X-ray detection signal outputted from each radiation detection element in all the areas is inputted to one signal processing device 93 that is connected to all the radiation detection elements of the FPD 82A. This signal processing device 93 integrates the X-ray detection signal outputted from each radiation detection element at preselected time intervals to obtain X-ray intensity information about each radiation detection element. A position code for each radiation detection element in the FPD 82A is attached to the X-ray intensity information. The resultant X-ray intensity information is stored in the memory 100 from the input interface 97. Consequently, the X-ray intensity information is associated with the position codes of the radiation detection elements.

Further, each radiation detection element in all the areas of the FPD 82B, which has detected the X-rays 84B, outputs an X-ray detection signal. The X-ray detection signal outputted from each radiation detection element in all the areas is inputted to the other signal processing device 93 that is connected to all the radiation detection elements of the FPD 82B. This other signal processing device 93 integrates the X-ray detection signal outputted from each radiation detection element at preselected time intervals to obtain X-ray intensity information about each radiation detection element. A position code for each radiation detection element in the FPD 82B is attached to the X-ray intensity information. The resultant X-ray intensity information is stored in the memory 100 from the input interface 97.

In the first imaging mode, which is used for the head 79A, the imaging mode information stored in the memory 100 is small FOV information. Therefore, the X-ray intensity acquisition device 98 acquires, from the memory 100, the X-ray intensity information to which the position code for each radiation detection element in the small FOV areas R1 of the FPDs 82A, 82B is attached. The X-ray intensity acquisition device 98 additionally acquires the offset amount OS stored in the memory 100. The X-ray intensity acquisition device 98 outputs, to the correction device 98A, the whole X-ray intensity information and offset amount OS concerning the small FOV areas R1, which are acquired from the memory 100.

The correction device 98A uses the offset amount OS to correct the position information concerning the X-ray intensity information to which the position codes in the small FOV areas R1 are attached. The correction device 98A obtains position information $((X_i-OS), Y_j)$ by correcting the position information $(X_i, Y_j)$ about each radiation detection element $P_{ij}$ in the small FOV area R1 of the FPD 82B. The corrected information is expressed by $P_{ij}$ $((X_i-OS), Y_j)$. Meanwhile, the position information $(X_i, Y_j)$ about each radiation detection element $P_{ij}$ in the small FOV area R1 of the FPD 82A is corrected to obtain position information $((X_i+OS), Y_j)$. The corrected information is expressed by $P_{ij}$ $((X_i+OS), Y_j)$.

The correction device 98A outputs, to the image reconstruction device 99, the X-ray intensity information to which the corrected position information is attached, that is, the X-ray intensity information $P_{ij}$ $((X_i-OS), Y_j)$ and the X-ray intensity information $P_{ij}$ $((X_i+OS), Y_j)$. The image reconstruction device 99 inputs the rotation angle of the rotary gantry 31, which is measured by the angle detector 54A, in addition to the X-ray intensity information that concerns each radiation detection element in the small FOV areas R1 of the FPDs 82A, 82B and includes the corrected position information. Tomographic image information (current tomographic image information) covering the diseased part of the head of the patient 79 is generated by using the X-ray intensity information $P_{ij}$ $((X_i-OS), Y_j)$, the X-ray intensity information $P_{ij}$ $((X_i+OS), Y_j)$, and each measured rotation angle (refer to Paragraph 0037 of Japanese Patent Application Laid-Open No. 2006-239403).

The generated current tomographic image information is inputted from the image reconstruction device 99 to the positioning information generation device 95. Three-dimensional tomographic image information (reference tomographic image information) obtained by preceding X-ray CT imaging (reference X-ray CT imaging) is inputted in advance to the positioning information generation device 95 and stored in a memory (not shown). Based on the current tomographic image information and the reference tomographic image information, the positioning information generation device 95 calculates the X-direction and Y-direction movement amounts of the bed 65, which is bed positioning information concerning the X-Y plane, the rotation angle of the bed 65, and the Z-direction movement amount of the bed 65, which is the bed positioning information concerning the X-Z plane (refer to Paragraphs 0040 to 0044 of Japanese Patent Application Laid-Open No. 2006-239403).

The movement amounts of the bed and the rotation angle of the bed 65, which are calculated by the positioning information generation device 95, are inputted to the bed control device 91. Based on the inputted X-, Y-, and Z-direction movement amounts of the bed 65 and on the inputted rotation angle of the bed 65, the bed control device 91 moves the bed 65 by controlling the associated drive mechanisms of the treatment table 64 (refer to Paragraph 0045 of Japanese Patent Application Laid-Open No. 2006-239403). In the above-described manner, the diseased part in the head 79A of the patient 79 on the bed 65 is positioned to match the isocenter 83 at the point of intersection between the central axis 78 of the irradiation device 60 and the central axis 29 of the rotary gantry 31. This concludes the positioning of the diseased part in the head 79A. After the diseased part is positioned, the particle beam therapy system 1 irradiates the diseased part with an ion beam to treat the diseased part with the ion beam.

Irradiating the diseased part of the patient 79 with a particle beam, such as a proton ion beam (or a carbon ion beam), in accordance with the present embodiment will now be summarized. The proton ion beam is hereinafter simply referred to as the ion beam.

Therapy plan information obtained from therapy planning conducted before cancer therapy based on the ion beam is inputted before the start of therapy from the therapy planning device 107 and stored in the database 106 of the control system 84C. The therapy plan information includes the direction of ion beam irradiation, the number of layers, the number of irradiation spots in each layer, the position of each irradiation spot in a layer, a target dose for each irradiation spot, the irradiation order of irradiation spots in a layer, and the ion beam energy for each layer. The CPU 86 of the central control device 85 reads the therapy plan information from the database 106 and stores the read therapy plan information in the memory 87. Further, the CPU 86 reads spot irradiation parameters (the number of layers, the number of irradiation spots in each layer, the position of each irradiation spot in a layer, a target dose for each irradiation spot, and the irradiation order of irradiation spots in a layer) from the memory 87 and outputs the read spot irradiation parameters to the scanning control device 89. The spot irradiation parameters are stored in a memory 89A of the scanning control device 89.

Before the diseased part is irradiated with the ion beam, the first gantry control device 123A outputs a rotation command to drive the rotation device 52. When the rotation device 52 is driven, the rotary gantry 31 rotates to orient the central axis 78 of the irradiation device 60 in an ion beam irradiation direction specified by a therapy plan. The rotary gantry 31 rotates at a speed of approximately 1 min$^{-1}$. The agreement between the central axis 78 of the irradiation device 60 and the ion beam irradiation direction is confirmed based on the rotation angle of the rotary gantry 31, which is measured by the angle detector 54A. When the central axis 78 of the irradiation device 60 agrees with the ion beam irradiation direction, the first gantry control device 123A outputs a rotation stop command to stop the drive of the rotation device 52. This also stops the rotation of the rotary gantry 31.

When the rotary gantry 31 rotates to rotate the irradiation device 60 to face the ion beam irradiation direction, the ring rail drive device 55 is driven to rotate the movable ring rail 48B in a direction opposite to the direction of rotation of the rotary gantry 31. Therefore, the movable ring rail 48B looks as if it is stopped. Consequently, when the rotary gantry 31 rotates to rotate the irradiation device 60, the movable floor 39 whose opposite ends are movably attached to the pair of guide rails 62 attached to the pair of opposing lateral surfaces of the irradiation device 60 by the slide members 63A, 63B moves along the semicylindrical track 102.

After the rotation of the rotary gantry 31 is stopped, ions (e.g., protons) generated by the ion source are injected into the linear accelerator 14 and accelerated. An ion beam emitted from the linear accelerator 14 is passed through the injector 5 and injected into the circular beam duct 4 of the synchrotron accelerator 3. While circulating in the beam duct 4, the ion beam is accelerated to an energy (e.g., 200 MeV) required for the ion beam to reach, for example, the deepest one of diseased part layers in the direction of ion beam irradiation. Under normal conditions, the energy of the ion beam used for diseased part treatment is set to be within a range of 100 to 200 MeV. More specifically, it is set based on the depth of each diseased part layer from the body surface.

The ion beam is irradiated, for example, in order from the deepest layer from the body surface to the shallowest layer. The scanning control device 89 controls the scanning electromagnets 74, 75 to set an ion beam irradiation position to an irradiation spot in the deepest layer. After the ion beam irradiation position is set, the scanning control device 89 outputs a beam irradiation start signal to the accelerator/transport system control device 88. Upon receipt of the beam irradiation start signal, the accelerator/transport system control device 88 outputs a switch ON command. The switch ON command closes the open/close switch 12 so that a high-frequency voltage from the high-frequency power supply 11 is applied from the ejection high-frequency electrode 10 to the ion beam circulating in the beam duct 4. As a result, the circulating ion beam is irradiated from the synchrotron accelerator 3 into the beam path 16 through the septum electromagnet 13. When the ion beam is irradiated from the synchrotron accelerator 3, the shutter 28 is extracted from the beam path 16. The irradiated ion beam passes through the beam paths 16, 18 and reaches the irradiation device 60. Having arrived in the irradiation device 60, the ion beam is irradiated onto an irradiation spot in the aforementioned layer of the diseased part in the head that is set by the scanning electromagnets 74, 75.

While the ion beam is irradiated onto the diseased part of the head with the central axis 78 of the irradiation device 60 oriented in a predetermined ion beam irradiation direction, the X-rays 84A emitted from the X-ray source 80A and the X-rays 84B emitted from the X-ray source 80B are both irradiated onto the diseased part of the patient 79 on the bed 65. The X-rays 84A transmitted through the head of the patient 79 are detected by the radiation detection elements of the FPD 82A, and the X-rays 84B transmitted through the same head are detected by the radiation detection elements of the FPD 82B.

As is the case with the aforementioned diseased-part positioning, one signal processing device 93 connected to all the radiation detection elements of the FPD 82A acquires the X-ray intensity information based on the X-ray detection signal of each radiation detection element. Based on the whole X-ray intensity information acquired by the signal processing device 93 and on the measured rotation angle of the rotary gantry 31, the image reconstruction device 99 generates first two-dimensional image information about the diseased part in a plane orthogonal to the irradiation direction of the X-rays 84A from the X-ray source 80A. The plane orthogonal to the irradiation direction of the X-rays 84A from the X-ray source 80A is a plane orthogonal to the direction of the central axis 29 of the rotary gantry 31 at an angle that is obtained by adding 135 degrees to the measured rotation angle of the rotary gantry 31 (the angle of the central axis 78 of the irradiation device 60).

As is the case with generation of the first two-dimensional image information about the diseased part, based on the whole X-ray intensity information acquired by the other signal processing device 93 connected to all the radiation detection elements of the FPD 82B and on the measured rotation angle of the rotary gantry 31, the image reconstruction device 99 generates second two-dimensional image information about the diseased part in a plane orthogonal to the irradiation direction of the X-rays 84B from the X-ray source 80B. The plane orthogonal to the irradiation direction of the X-rays 84B from the X-ray source 80B is a plane orthogonal to the direction of the central axis 29 of the rotary gantry 31 at an angle that is obtained by adding 225 degrees to the measured rotation angle of the rotary gantry 31 (the angle of the central axis 78 of the irradiation device 60).

Based on the first two-dimensional image information and the second two-dimensional image information, the size and shape of the diseased part of the head can be determined during ion beam irradiation. Observing changes in the size and shape of the diseased part since the beginning of ion beam irradiation onto to the diseased part makes it possible to confirm the effect of therapy provided by irradiating the diseased part with the ion beam.

Further, the first two-dimensional image information and the second two-dimensional image information, which are generated by the image reconstruction device 99, are inputted to the positioning information generation device 95. Based on the reference tomographic image information, the first two-dimensional image information, and the second two-dimensional image information, the positioning information generation device 95 calculates the amount of deviation of the diseased part irradiated with the ion beam from the reference tomographic image information. The current position of the diseased part irradiated with the ion beam can be confirmed based on the calculated deviation amount.

While an irradiation spot in the aforementioned layer of the diseased part is irradiated with the ion beam, the dose monitor 77 measures the dose administered to the irradiation spot since the beginning of ion beam irradiation onto the irradiation spot. When a target dose is reached by the dose administered to the irradiation spot, which is measured by the dose monitor 77, the scanning control device 89 outputs a beam irradiation stop signal to the accelerator/transport system control device 88. Upon receipt of the beam irradiation stop signal, the accelerator/transport system control device 88 outputs a switch OFF signal to the open/close switch 12. The open/close switch 12 is then opened to stop the application of the high-frequency voltage from the high-frequency power supply 11 to the ejection high-frequency electrode 10. This stops the irradiation of the ion beam from the synchrotron accelerator 3.

Subsequently, the ion beam is sequentially irradiated onto the remaining irradiation spots in the layer. When the ion beam irradiation onto all the irradiation spots in the layer is completed, the ion beam is sequentially irradiated onto all irradiation spots in all the remaining layers in order from the deepest layer to the shallowest layer.

A therapy provided by irradiating the ion beam onto the diseased part in the head has been described above. A therapy provided by irradiating the ion beam onto a cancer-affected part in the trunk of a patient is described below.

As is the case with the head, first of all, current X-ray CT imaging is performed on the vicinity of a diseased part of the trunk. The drive mechanisms of the treatment table 64 are driven to roughly position the diseased part in the trunk of the patient 79 on the bed 65. When the diseased part to be irradiated is in the trunk 79B (see FIG. 12B) of the patient 79, "trunk", which is a radiation target, and a dimension of the trunk 79B of the patient 79 in the width direction of the bed 65 (the width of the trunk) are inputted to the input device 101. The radiation target, namely, "trunk", and information about the width of the trunk 79B are used as large FOV information (second imaging mode information), which serves as the imaging mode information and is stored in the memory 100 through the input interface 97. The trunk 79B is a greater radiation target than the head and neck.

After the diseased part is completely positioned, the X-ray irradiation start command inputted from the input device 101 is inputted to the X-ray source control device 92 and to the collimator control device 96. Upon receipt of the X-ray irradiation start command, the collimator control device 96 exercises control based on the large FOV information read from the memory 100 in order to adjust the size of the aperture 121 by driving the transport devices 122A, 122B, 122C, 122D of the collimators 81A, 81B. The aperture 121 is adjusted so that X-rays transmitted through the trunk 79B are sized so as to be incident on the large FOV areas R2 of the FPDs 82A, 82B. The X-ray filter 125 attached to the diaphragm member 120D covers the aperture 121 from the underside of the diaphragm member 120D.

After the aperture 121 is set so that the X-rays are incident on the large FOV areas R2, the diaphragm member setup completion information is inputted from the collimator control device 96 to the X-ray source control device 92 and the second gantry control device 123B. Upon receipt of the diaphragm member setup completion information, the X-ray source control device 92, which has already received the X-ray irradiation start command, outputs the X-ray irradiation command. As a result, X-rays are emitted from both the X-ray sources 80A, 80B. Further, upon receipt of the diaphragm member setup completion information, the second gantry control device 123B outputs, to the rotation device 52 of the rotary gantry 31, a rotation command for rotating the rotary gantry 31 within an angular range, for example, of 0 to 360 degrees based on the large FOV information. Thus, the rotary gantry 31 rotates 0 to 360 degrees. More specifically, the rotary gantry 31 first rotates within an angular range of 0 to 180 degrees, then returns to 0 degrees, and rotates within the remaining angular range of 0 to −180 degrees.

Figure 12B:
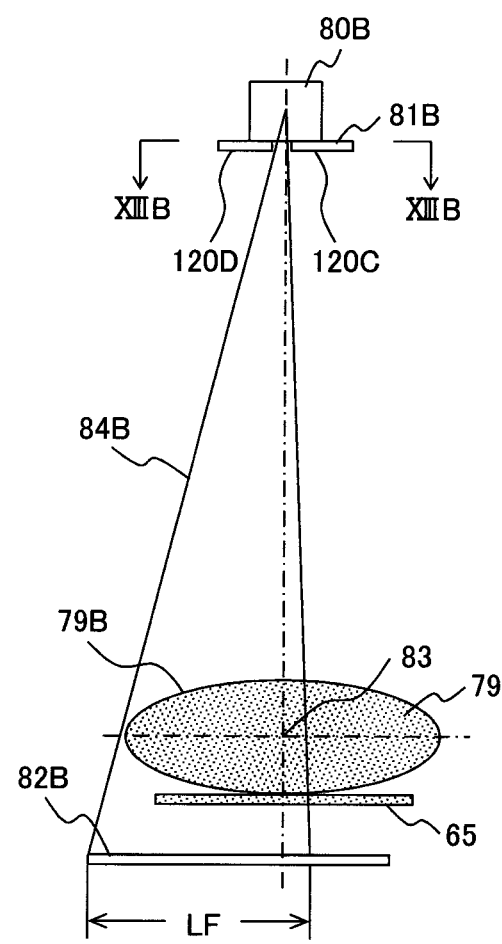
FIG. 12B is a diagram illustrating how X-rays are emitted from an X-ray source to a radiation target (large FOV) and how X-rays transmitted through the radiation target (large FOV) are detected.

Current X-ray CT imaging is performed on the trunk 79B in the second imaging mode while rotating the rotary gantry 31. FIG. 12 B illustrates a state where the X-rays 84B emitted from the X-ray source 80B fall on the trunk 79B to let the FPD 82B detect the X-rays 84B transmitted through the trunk 79B. A state where the FPD 82A detects the X-rays 84A emitted from the X-ray source 80A is substantially the same as the state illustrated in FIG. 12B except that the small FOV area R1 having a length of SF and the large FOV area R2 having a length of LF are left-right reversed.

While the rotary gantry 31 is rotated, the X-rays 84A, 84B are irradiated onto the diseased part of the trunk 79B of the patient 79. The X-rays 84A emitted from the X-ray source 80A are passed through the aperture 121 (FIG. 13B), which is set in the collimator 81A, forwarded through the X-ray filter 125, passed through the through hole 103A, transmitted through the X-ray transmission portion 44 of the X-ray transmission plate 42B, and irradiated onto the diseased part of the trunk 79B and onto the vicinity of the diseased part. The X-rays 84A transmitted through the trunk 79B are detected by the radiation detection elements in the large FOV area R2 of the FPD 82A (see FIG. 12B). Further, the X-rays 84B emitted from the X-ray source 80B are passed through the aperture 121 (FIG. 13B), which is set in the collimator 81B, transmitted through the X-ray filter 125, forwarded through the through hole 103B, transmitted through the X-ray transmission portion 44 of the X-ray transmission plate 42A, and irradiated onto the diseased part of the trunk 79B and onto the vicinity of the diseased part. The X-rays 84B transmitted through the trunk 79B are detected by the radiation detection elements in the large FOV area R2 of the FPD 82B (see FIG. 12B).

When the rotary gantry 31 is rotated 360 degrees, the second gantry control device 123B outputs the rotation stop command to the rotation device 52. This stops the rotation of the rotation of the rotary gantry 31. Upon receipt of the rotation stop command, the X-ray source control device 92 outputs the X-ray emission stop command to the X-ray sources 80A, 80B. This stops the X-ray emission from the X-ray sources 80A, 80B so as to stop the X-ray irradiation onto the diseased part of the trunk 79B.

The X-ray detection signal outputted from each radiation detection element in all the areas of the FPD 82A, which has detected the X-rays 84A, and from each radiation detection element in all the areas of the FPD 82B, which has detected the X-rays 84B, is inputted to one signal processing device 93 for the FPD 82A and to the other signal processing device 93 for the FPD 82B. As is the case with the aforementioned head 79A, these signal processing devices 93 separately acquire the X-ray intensity information about each radiation detection element in the FPDs 82. A position code for each radiation detection element in the FPDs 82A, 82B attached to the X-ray intensity information. The resultant X-ray intensity information is stored in the memory 100 from the input interface 97.

In the second imaging mode, which is used for the trunk 79B, the imaging mode information stored in the memory 100 is large FOV information. Therefore, the X-ray intensity acquisition device 98 acquires, from the memory 100, the X-ray intensity information $P_{ij}$ ($X_i$, $Y_j$) to which the position code for each radiation detection element in the large FOV areas R2 of the FPDs 82A, 82B is attached. The correction device 98A uses the offset amount OS to correct the position information concerning the X-ray intensity information to which the position codes in the large FOV areas R2 are attached. The correction device 98A obtains position information (($X_i$−OS), $Y_j$) by correcting the position information ($X_i$, $Y_j$) about each radiation detection element $P_{ij}$ in the large FOV area R1 of the FPD 82B. The corrected information is expressed by $P_{ij}$ (($X_i$−OS), $Y_j$). Meanwhile, the position information ($X_i$, $Y_j$) about each radiation detection element $P_{ij}$ in the large FOV area R2 of the FPD 82A is corrected to obtain position information (($X_i$+OS), $Y_j$). The corrected information is expressed by $P_{ij}$ (($X_i$+OS), $Y_j$).

The correction device 98A outputs, to the image reconstruction device 99, the X-ray intensity information to which the corrected position information is attached, that is, the X-ray intensity information $P_{ij}$ (($X_i$−OS), $Y_j$) and the X-ray intensity information $P_{ij}$ (($X_i$+OS), $Y_j$). As is the case with the aforementioned head, the image reconstruction device 99 generates the tomographic image information (current tomographic image information), which covers the diseased part of the trunk 79B of the patient 79, by using not only the X-ray intensity information $P_{ij}$ (($X_i$−OS), $Y_j$) and X-ray intensity information $P_{ij}$ (($X_i$+OS), $Y_j$) about each radiation detection element in the large FOV areas R2 of the FPDs 82A, 82B, but also each of the measured rotation angles of the rotary gantry 31.

The generated current tomographic image information is inputted from the image reconstruction device 99 to the positioning information generation device 95. As is the case with the aforementioned head 79A, the positioning information generation device 95 calculates the movement amounts of the bed 65 and the rotation angle of the bed 65 based on the current tomographic image information and the reference tomographic image information. Based on the calculated movement amounts and rotation angle of the bed 65, the bed control device 91 moves the bed 65 by controlling the associated drive mechanisms of the treatment table 64. In the above-described manner, the diseased part in the trunk 79B of the patient 79 on the bed 65 is positioned to match the isocenter 83 at the point of intersection between the central axis 78 of the irradiation device 60 and the central axis 29 of the rotary gantry 31. This concludes the positioning of the diseased part in the trunk 79B.

After the diseased part is positioned, the particle beam therapy system 1 irradiates the diseased part with an ion beam to treat the diseased part in the trunk 79B with the ion beam. Ion beam irradiation onto the diseased part in the trunk 79B is performed in the same manner as ion beam irradiation onto the diseased part in the aforementioned head 79A.

The following describes operations that are performed by the connection member 61 for the irradiation device 60 and by the footboard groups 41A, 41B including the slide members 63A, 63B and the pair of guide rails 62.

FIG. 11 illustrates the cross-sectional shape of the movable floor 39 of the therapy cage 38 in a state where the irradiation device 60 is positioned directly above the bed 65. The state illustrated in FIG. 11 is regarded as the reference state where the rotation angle of the rotary gantry 31 is 0 degrees. The slide members 63A, 63B for the irradiation device 60, which are movably attached to the pair of guide rails 62 disposed respectively on the pair of lateral surfaces opposing each other in the rotation direction of the rotary gantry 31 and are respectively attached to one end of the footboard groups 41a, 41B, are both at the farthest position from the central axis 29 of the rotary gantry 31 in the radial direction of the rotary gantry 31 when the rotation angle of the rotary gantry 31 is 0 degrees.

The concept of inner wall length defined in the present embodiment will now be described. In the therapy cage 38, the overall length of each semicylindrical track 102 is fixed (invariable). The arc portion and the horizontal portion are formed over a length that is obtained by subtracting the length corresponding to the irradiation device 60 from the overall length of the semicylindrical track 102. The length corresponding to the irradiation device 60 is the length of the irradiation device 60 that is measured between the slide members 63A movably attached to the guide rails 62 disposed on the pair of lateral surfaces opposing each other in the rotation direction of the rotary gantry 31. The inner wall length is defined as the length of a range corresponding to the arc and horizontal portions of the semicylindrical track 102. That is to say, the inner wall length is the difference between the overall length of the semicylindrical track 102 and the length corresponding to the irradiation device 60. At the same time, the inner wall length substantially corresponds to the sum of the lengths of the footboard groups 41a, 41B, 41C, the widths of the X-ray transmission plates 42A, 42B, and the length of the opening 104.

If a circular track for guiding the movable floor 39 is formed on each of the stationary ring rail 48A and movable ring rail 48B of the therapy cage, the inner wall length is fixed irrespective of the rotation angle of the rotary gantry 31. However, the track 102 formed on each of the stationary ring rail 48A and movable ring rail 48B is semicylindrical in shape. Thus, the inner wall length varies with the rotation angle of the rotary gantry 31. That is to say, as the length corresponding to the irradiation device 60 varies with the rotation angle of the rotary gantry 31, the inner wall length varies with the rotation angle.

While the irradiation device 60 is on the arc portion of the semicylindrical track 102 (the rotation angle of the rotary gantry 31 is within a range of 0 to 90 degrees), the length corresponding to the irradiation device 60 is fixed and thus the inner wall length is fixed. However, the length of the irradiation device 60 between the slide member 63A attached to one end of the footboard group 41A and the slide member 63A attached to one end of the footboard group 41B (the length corresponding to the irradiation device 60) decreases with a decrease in the distance to an end on the rotation axis side of the irradiation device 60. Therefore, when a part of the irradiation device 60 moves to the coupling portion of the semicylindrical track 102 (the rotation angle of the rotary gantry 31 is within a range of 90 to 120 degrees), and then moves to the horizontal portion (the rotation angle of the rotary gantry 31 is within a range of 120 to 180 degrees), the length corresponding to the irradiation device 60 varies and thus the inner wall length varies.

When the movable floor 39 moves along the semicylindrical track 102 in accordance with the rotation angle of the rotary gantry 31, the slide members 63A, 63B for the irradiation device 60, which are movably attached respectively to the pair of guide rails 62 disposed on the pair of lateral surfaces opposing each other in the rotation direction of the rotary gantry 31, move in the radial direction of the rotary gantry 31 along the guide rails 62 in accordance with the movement of the movable floor 39, that is, the rotation of the irradiation device 60. The above-described variation in the inner wall length occurs when the slide members 63A, 63B move in the radial direction of the rotary gantry 31 along the guide rails 62.

When, for example, the rotation angle of the rotary gantry 31 is 180 degrees and the irradiation device 60 is positioned on the horizontal portion (see FIG. 17), the slide members 63A, 63B for the irradiation device 60, which are movably attached respectively to the pair of guide rails 62 disposed on the pair of lateral surfaces opposing each other in the rotation direction of the rotary gantry 31 and are respectively attached to one end of the footboard groups 41A, 41B, are both at the nearest position from the central axis 29 of the rotary gantry 31 in the radial direction of the rotary gantry 31. In this instance, the length of the irradiation device 60 between the slide member 63A attached to one end of the footboard group 41A and the slide member 63A attached to one end of the footboard group 41B is less than when the rotation angle of the rotary gantry 31 is 0 degrees and the irradiation device 60 is positioned on the arc portion (see FIG. 11).

Figure 17:
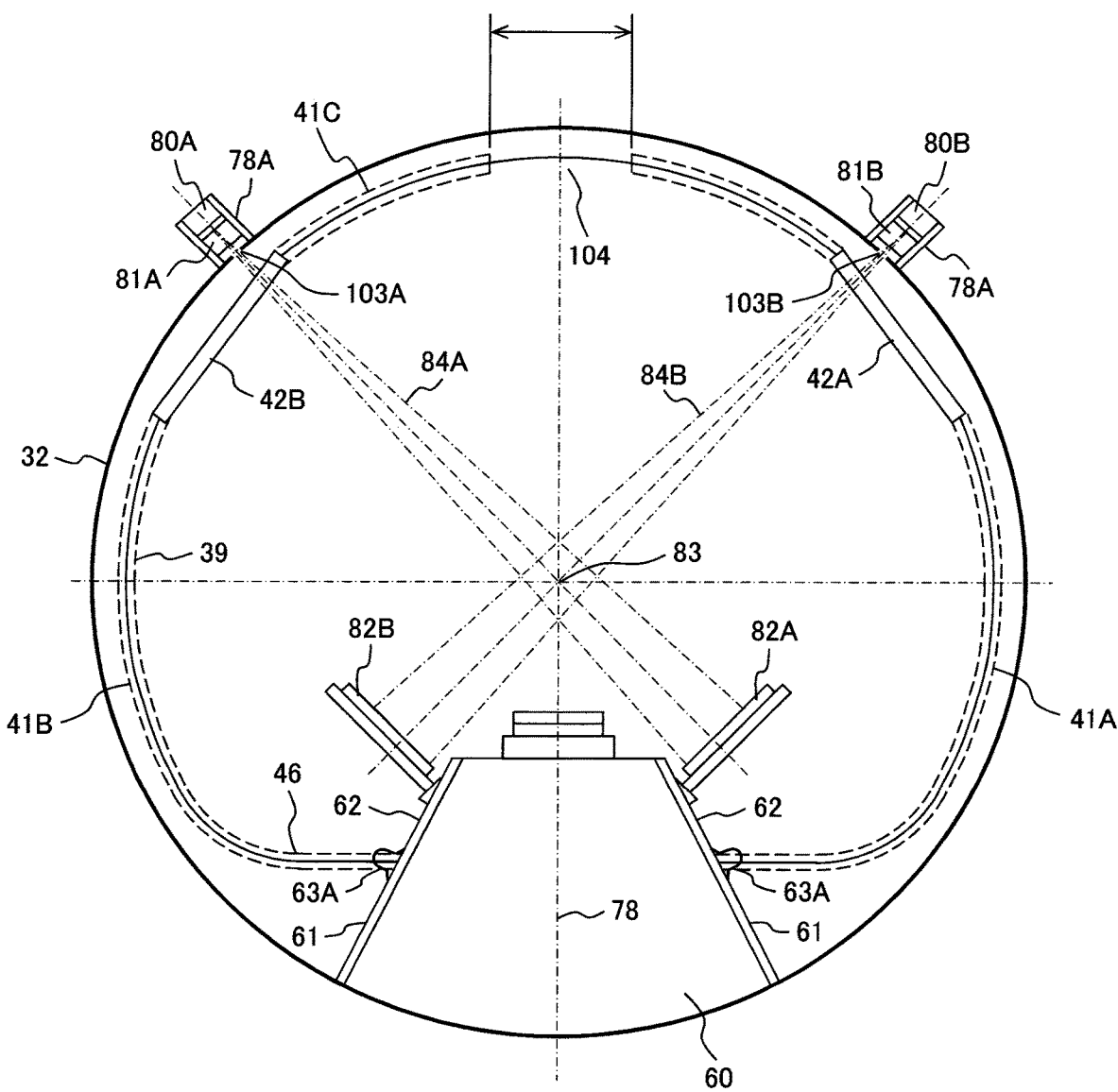
FIG. 17 is a diagram illustrating the status of the movable floor of the radiotherapy cage when the rotation angle of the rotary gantry shown in FIGS. 2 and 3 is 180 degrees.

When the irradiation device 60 moves from a rotation angle of 0 degrees to a rotation angle of 180 degrees due to the rotation of the rotary gantry 31, the slide members 63A, 63B attached respectively to one end of the footboard groups 41A, 41B move along the guide rails 62 and in the direction of the central axis 29 of the rotary gantry 31 (see FIG. 17).

Inner wall length changes caused by changes in the rotation angle of the rotary gantry 31 occur in coordination with the movement of the slide members 63A, 63B along the guide rails 62 and with the changes in the length of the opening 104.

When the slide members 63A, 63B are at the farthest position from the central axis 29 of the rotary gantry 31 in the radial direction of the rotary gantry 31, that is, the irradiation device 60 is at an angular position of 0 degrees (FIG. 11), the opening 104 generated between a pair of neighboring footboards 40 of the footboard group 41C becomes narrower. In coordination with the generation of the opening 104, the cover take-up device 43 takes up the cover 42 to cover the opening 104. The opening 104 is positioned directly below the bed 65.

When the rotation angle of the rotary gantry 31 is 180 degrees, the irradiation device 60 is wholly positioned on the horizontal floor portion 46 of the semicylindrical track 102 (FIG. 17). In this instance, the opening 104 has the maximum length, but is positioned directly above the bed 65.

The fact that the medical technologist 105 can safely access the patient 79 at any rotation angle of the rotary gantry 31 will now be described while focusing on changes in the position and length of the opening 104 that are caused by changes in the rotation angle of the rotary gantry 31. When the rotation angle of the rotary gantry 31 is 0 degrees, the irradiation device 60 is positioned directly below the bed 65 (see FIG. 11). Therefore, the opening 104 does not cause any safety problem. When the rotation angle of the rotary gantry 31 is within a range of 0 and 60 degrees, the irradiation device 60 is positioned so as to generate the opening 104 in the horizontal floor portion 46 of the movable floor 39 and allow the footboard group 41C to form the horizontal floor portion 46. However, the opening 104 has a limited width due to a structural effect produced by the inclination of the irradiation device 60 (tapered). Thus, the opening 104 can be covered by the cover 42 and does not cause any safety problem. Further, when the rotation angle of the rotary gantry 31 is within a range of 60 and 180 degrees, the irradiation device 60 is positioned so that the opening 104 is not generated in the horizontal floor portion 46 of the movable floor 39. Therefore, no safety problem is caused by the opening 104.

As described above, the present embodiment permits the medical technologist 105 to stand on the horizontal floor portion 46 of the movable floor 39 and safely access the patient 79 at any rotation angle of the rotary gantry 31.

The signal processing devices 93 provided respectively for the FPDs 82A, 82B are connected to the radiation detection elements included in the respective FPDs.

In the present embodiment, the signal processing devices, the memory 100, and the X-ray intensity acquisition device 98 form an X-ray intensity information generation device 127 (see FIG. 10). The signal processing devices are connected to the radiation detection elements in the FPDs in order to generate the X-ray intensity information based on X-ray detection signals outputted from the radiation detection elements. The memory 100 stores the X-ray intensity information acquired by the signal processing devices. The X-ray intensity acquisition device 98 acquires the X-ray intensity information, which is obtained based on the output signals of the radiation detection elements in the associated FOV areas of the FPDs (either the small FOV areas or the large FOV areas), from the memory 100 in accordance with the imaging mode information (either the small FOV information or the large FOV information) inputted from the input device 101. Based on the output signals of the radiation detection elements of the FPDs, the X-ray intensity information generation device 127 generates multiple pieces of X-ray intensity information about the small or large FOV areas of the FPDs.

According to the present embodiment, three-dimensional tomographic image information can be reconstructed by using multiple pieces of X-ray intensity information derived from the X-ray detection signals outputted from the radiation detection elements in the small FOV areas (hereinafter referred to as the multiple pieces of X-ray intensity information about the small FOV areas), which are included in all the pieces of X-ray intensity information that are obtained based on the X-ray detection signals outputted from the radiation detection elements in the FPDs 82A, 82B when current X-ray CT imaging is performed on the diseased part in the head 79A. Further, different three-dimensional tomographic image information can be reconstructed by using multiple pieces of X-ray intensity information derived from the X-ray detection signals outputted from the radiation detection elements in the large FOV areas (hereinafter referred to as the multiple pieces of X-ray intensity information about the large FOV areas), which are included in all the pieces of X-ray intensity information that are obtained based on the X-ray detection signals outputted from the radiation detection elements in the FPDs 82A, 82B when current X-ray CT imaging is performed on the diseased part in the trunk 79B.

The X-ray intensity information generation device 127 is capable of generating the multiple pieces of X-ray intensity information about the small FOV areas based on the X-ray detection signals that are derived from current X-ray CT imaging performed on the diseased part in the head 79A and outputted from the radiation detection elements in the small FOV areas, which are included in all the radiation detection elements in the FPDs 82A, 82B mounted on the rotary gantry 31. The image reconstruction device 99 is capable of reconstructing the three-dimensional tomographic image information by using the multiple pieces of X-ray intensity information about the small FOV areas, which are generated by the X-ray intensity information generation device 127. Further, the X-ray intensity information generation device 127 is capable of generating the multiple pieces of X-ray intensity information about the large FOV areas based on the X-ray detection signals that are derived from current X-ray CT imaging performed on the diseased part in the trunk 79B and outputted from the radiation detection elements in the large FOV areas, which are included in all the radiation detection elements in the FPDs 82A, 82B mounted on the rotary gantry 31. The image reconstruction device 99 is capable of reconstructing the three-dimensional tomographic image information by using the multiple pieces of X-ray intensity information about the large FOV areas, which are generated by the X-ray intensity information generation device 127.

As described above, the three-dimensional tomographic image information is reconstructed by using the X-ray intensity information that is obtained based on the X-ray detection signals outputted from the radiation detection elements in the associated FOV areas, which is included in all the pieces of X-ray intensity information. Therefore, in contrast to a conventional method, the present embodiment eliminates the necessity of moving the FPDs. Consequently, the present embodiment does not require an FPD transport device, a control device for controlling the movement of such a transport device, and a monitoring device for monitoring whether the FPDs is moved and set at a predetermined position. As a result, the structure of the radiographic imaging apparatus, that is, the structure of the particle beam therapy system 1, can be simplified.

Further, as the FPDs need not be moved, the present embodiment saves the time required for moving the FPDs during current X-ray CT imaging. Consequently, the time required for current X-ray CT imaging is reduced to shorten the time required for a patient's cancer therapy.

When, in the present embodiment, current X-ray CT imaging is performed on the head 79A or the trunk 79B, all pieces of X-ray intensity information obtained based on the X-ray detection signals outputted from the radiation detection elements in the FPDs 82A, 82B are stored in the memory 100 of the imaging processing device 94. Thus, based on the imaging mode information (small FOV information or large FOV information) set by the input device 101, the X-ray intensity information about the associated FOV areas (either the multiple pieces of X-ray intensity information about the small FOV areas or the multiple pieces of X-ray intensity information about the large FOV areas) can be acquired from the memory 100. Therefore, the three-dimensional tomographic image information can easily be reconstructed for the head 79A or the trunk 79B by using the multiple pieces of X-ray intensity information about the small FOV areas or the multiple pieces of X-ray intensity information about the large FOV areas.

The second gantry control device 123B is capable of changing the rotation angle of the rotary gantry 31 in accordance with the imaging mode information. When current X-ray CT imaging is performed with small FOV information set as the imaging mode information, the second gantry control device 123B outputs a rotation command for rotating the rotary gantry 31 within an angular range of 0 to 200 degrees. Therefore, the time required for performing current X-ray CT imaging on the head 79A can be reduced. In addition, more distinct three-dimensional tomographic image information about the head 79A can be acquired. When current X-ray CT imaging is performed with large FOV information set as the imaging mode information, the second gantry control device 123B outputs a rotation command for rotating the rotary gantry 31 within an angular range of 0 to 360 degrees. Therefore, more distinct three-dimensional tomographic image information about the trunk 79B can be acquired.

As the diaphragm members of the collimators 81A, 81B are moved based on the set FOV information, X-rays can be irradiated onto the patient 79 in association with the small FOV areas R1 or the large FOV areas R2 of the FPDs 82A, 82B. This makes it easy to acquire the multiple pieces of X-ray intensity information about the small FOV areas and the multiple pieces of X-ray intensity information about the large FOV areas.

In the present embodiment, the X-ray filter 125 is attached to one diaphragm member 120D of each collimator 81A, 81B and set for the FPD side of the aperture 121 by moving the diaphragm member 120D. This significantly reduces not only the amount of X-rays 84A that are emitted from the X-ray source 80A and directly incident on the FPD 82A without being transmitted through the patient 79, but also the amount of X-rays 84B that are emitted from the X-ray source 80B and directly incident on the FPD 82B without being transmitted through the patient 79. When large amounts of X-rays are directly incident on an FPD without being transmitted through the patient 79, the reconstructed three-dimensional tomographic image information degrades in image quality because the dynamic range of the patient 79 is relatively narrow. Applying the X-ray filter 125 significantly reduces the amount of X-rays that are directly incident on the FPD without being transmitted through the patient 79. Thus, the application of the X-ray filter 125 improves the image quality of the reconstructed three-dimensional tomographic image information. Further, as the X-ray filter 125 is attached to and integrated with the diaphragm member 120D, the necessity for a drive mechanism dedicated to the X-ray filter is eliminated. Consequently, the structure of the radiographic imaging apparatus can be further simplified.

The X-ray filter 125 is used to alleviate the saturation of X-rays in the FPD with respect to a portion (the vicinity of the body surface) where X-rays are transmitted through a small portion of the body of the patient 79. Therefore, the aperture 121 need not be entirely covered. The saturation of X-rays can be alleviated when the vicinity of an edge portion of the diaphragm member 120D is covered by the X-ray filter 125.

When X-ray imaging is performed in the first imaging mode, the position information $((X_i-OS), Y_j)$ about the radiation detection elements $P_{ij}$ in the small FOV area R1 of the FPD 82B and the position information (($X_i$+OS), $Y_j$) about the radiation detection elements $P_{ij}$ in the small FOV area R1 of the FPD 82A are acquired after the correction by the correction device 98A. Meanwhile, when X-ray imaging is performed in the second imaging mode, the position information (($X_i$−OS), $Y_j$) about the radiation detection elements $P_{ij}$ in the large FOV area R2 of the FPD 82B and the position information (($X_i$+OS), $Y_j$) about the radiation detection elements $P_{ij}$ in the large FOV area R2 of the FPD 82A are acquired after the correction by the correction device 98A. As the X-ray intensity information $P_{ij}$ (($X_i$−OS), $Y_j$) and X-ray intensity information $P_{ij}$ (($X_i$+OS), $Y_j$) to which the corrected position information about the radiation detection elements $P_{ij}$ is attached is inputted to the image reconstruction device 99, highly accurate three-dimensional tomographic image information based on the offset amount OS can be acquired.

The X-ray sources 80A, 80B are mounted on the rotary drum 32 of the rotary gantry 31, and the FPDs 82A, 82B are mounted on the irradiation device 60 so as to respectively face the X-ray sources 80A, 80B. Therefore, when, for example, the diseased part is to be positioned for X-ray imaging of the diseased part, the X-ray sources 80A, 80B and the FPDs 82A, 82B need not be moved in the axial direction of the rotary gantry 31. This reduces the time required for the start of X-ray imaging of the diseased part, and thus increases treatment throughput. In such X-ray imaging, the X-rays 84A, 84B emitted respectively from the X-ray sources 80A, 80B can be transmitted respectively through the X-ray transmission plates 42A, 42B of the movable floor 39 and irradiated onto the patient 79 on the bed 65.

In the particle beam therapy system described in Japanese Patent Application Laid-Open No. 2006-239403, the position of a diseased part cannot be confirmed while irradiating the diseased part with an ion beam because the employed irradiation device includes an X-ray source (X-ray tube). However, the particle beam therapy system 1 according to the present embodiment is configured so that the X-ray sources 80A, 80B are mounted on the rotary gantry 31. Therefore, while the diseased part is irradiated with an ion beam, the X-rays 84A, 84B emitted respectively from the X-ray sources 80A, 80B can be oriented in two different directions and irradiated onto the diseased part. Further, the X-rays 84A, 84B transmitted through the diseased part can be detected by the FPDs 82A, 82B. The tomographic image information about the diseased part of the patient 79 on the bed 65, which is irradiated with an ion beam from the irradiation device 60, can be generated by using the X-ray detection signals outputted from the radiation detection elements in the FPDs 82A, 82B. The position of the diseased part irradiated with an ion beam can be confirmed by using the tomographic image information. As the X-rays 84A, 84B oriented in two different directions are irradiated onto the diseased part, the position of the diseased part irradiated with an ion beam can be accurately determined. Further, changes in the size of the diseased part irradiated with an ion beam can be confirmed by using the tomographic image information. Therefore, the effect of therapy provided by ion beam irradiation can be confirmed.

The X-ray sources 80A, 80B and the collimators 81A, 81B may be attached to the inner surface of the rotary drum 32 and disposed outside the movable floor 39. Even when the X-ray sources 80A, 80B and the collimators 81A, 81B are disposed in the above manner, patient positioning data can be acquired. This also makes it possible to confirm the position of the diseased part irradiated with an ion beam and confirm changes in the size of such a diseased part.

In the present embodiment, the X-ray sources 80A, 80B are attached to the outer surface of the rotary drum 32 of the rotary gantry 31. Therefore, the gap between the movable floor 39 and the inner surface of the rotary drum 32 can be made smaller than when the X-ray sources 80A, 80B are attached to the inner surface of the rotary drum 32. This makes it possible to reduce the diameter of the rotary gantry 31. As a result, the rotary gantry 31 can be made compact.

The X-rays 84A emitted from the X-ray source 80A attached to the outer surface of the rotary drum 32 are transmitted through the through hole 103A in the rotary drum 32 and the X-ray transmission portion 44 of the X-ray transmission plate 42B, and then irradiated onto the diseased part of the patient 79. Thus, the emitted X-rays 84A can be irradiated onto the patient 79 without being blocked. Therefore, a clear image of the vicinity of the diseased part can be obtained by using the compact X-ray source 80A. The X-rays 84B emitted from the X-ray source 80B attached to the outer surface of the rotary drum 32 are transmitted through the through hole 103B in the rotary drum 32 and the X-ray transmission portion 44 of the X-ray transmission plate 42A, and then irradiated onto the diseased part of the patient 79. Therefore, the X-rays 84B emitted from the X-ray source 80B produce the same effect as the X-rays 84A emitted from the X-ray source 80A.

When the movable floor 39 moves along the track 102 due to the rotation of the rotary gantry 31, the X-ray transmission plates 42A, 42B of the movable floor 39 smoothly move along the track 102. This varies the positions of the X-ray transmission plates 42A, 42B in the track 102 in accordance with the rotation angle of the rotary gantry 31. Further, the portions of the X-ray transmission plates 42A, 42B through which the X-rays 84A, 84B are respectively transmitted are shifted in the circumferential direction of the rotary gantry 31 in accordance with the rotation angle of the rotary gantry 31. As the portions of the X-ray transmission plates 42A, 42B through which the X-rays are respectively transmitted are shifted in accordance with the rotation of the rotary gantry 31 as described above, the width $W_3$ of the X-ray transmission portion 44 in the circumferential direction of the rotary gantry 31 needs to be greater than the width $W_1$ of the footboards 40. As the width of the horizontal portion of the semicylindrical track 102 is $W_H$, the horizontal floor portion 46 of the movable floor 39, which is formed by the horizontal portion of the semicylindrical track 102, also has a width of $W_H$. The horizontal floor portion 46 needs to be formed in order to assure safety of the medical technologist 105 in the treatment room 54 and provide the medical technologist 105 with excellent accessibility to the patient on the bed 65. Consequently, the width $W_2$ of each of the X-ray transmission plates 42A, 42B needs to be equal to or smaller than $W_H$−$W_1$.

According to the present embodiment, the connection member 61, which includes the slide members 63A, 63B and the pair of guide rails 62, is used to connect the ends of the movable floor 39 respectively to the pair of lateral surfaces of the irradiation device 60, which oppose each other in the rotation direction of the rotary gantry 31. Therefore, the therapy cage 38 used in the present embodiment does not require a drive device, a control device, and their power source unlike a conventional radiotherapy cage (hereinafter referred to as the conventional therapy cage). Consequently, the therapy cage 38 used in the present embodiment is more simplified than the conventional therapy cage. The simplified therapy cage 38 according to the present embodiment reduces the possibility of failure and the amount of maintenance work.

In the present embodiment, when the rotary gantry 31 rotates, the slide members 63A, 63B, which are attached respectively to the ends of the movable floor 39, slide along the pair of guide rails 62 disposed respectively on the pair of lateral surfaces of the irradiation device 60, which oppose each other in the rotation direction of the rotary gantry 31, and move in the radial direction of the rotary gantry 31. Therefore, the medical technologist 105 can safely access the patient 79 on the bed 65 irrespective of the rotation angle of the rotary gantry 31. More specifically, the therapy cage according to the present embodiment is different from the conventional therapy cage in that the former eliminates the necessity of controlling a drive device to move an end of the movable floor toward the irradiation device or away from the irradiation device. Consequently, the present embodiment reduces the time required for one treatment to improve work efficiency.

In the present embodiment, the pair of lateral surfaces of the irradiation device 60, which oppose each other in the rotation direction of the rotary gantry 31, are tilted toward the tip of the irradiation device 60 so that the irradiation device 60 has a tapered structure. Meanwhile, an irradiation device 60A (indicated by a broken line in FIG. 18), which is used with a conventional particle beam therapy apparatus, is configured so that a pair of lateral surfaces of the irradiation device 60A, which oppose each other in the rotation direction of the rotary gantry 31, are in parallel with the rotation plane normal to the rotary gantry 31. A portion of the movable floor 39 that is positioned toward the footboard group 41A and between the slide members 63A, 63B and the opening 104 is referred to as the first movable floor portion, and a portion of the movable floor 39 that is positioned toward the footboard group 41B and between the slide members 63A, 63B and the opening 104 is referred to as the second movable floor portion. In the present embodiment, the total length of the first and second movable floor portions is greater than the total length of the first and second movable floor portions in the conventional particle beam therapy apparatus by length d (see FIG. 18). Therefore, when the irradiation device 60 is at a position where the rotation angle of the rotary gantry 31 is 150 degrees, the medical technologist 105 can approach the patient 79 by length d. This results in the improvement of work efficiency.

The present embodiment includes the X-ray source 80A, the collimator 81A, the through hole 103A, the X-ray transmission plate 42B, and the FPD 82A as well as the X-ray source 80B, the collimator 81B, the through hole 103B, the X-ray transmission plate 42A, and the FPD 82B. An alternative is to include either the X-ray source 80A, the collimator 81A, the through hole 103A, the X-ray transmission plate 42B, and the FPD 82A or the X-ray source 80B, the collimator 81B, the through hole 103B, the X-ray transmission plate 42A, and the FPD 82B.

Figure 19:
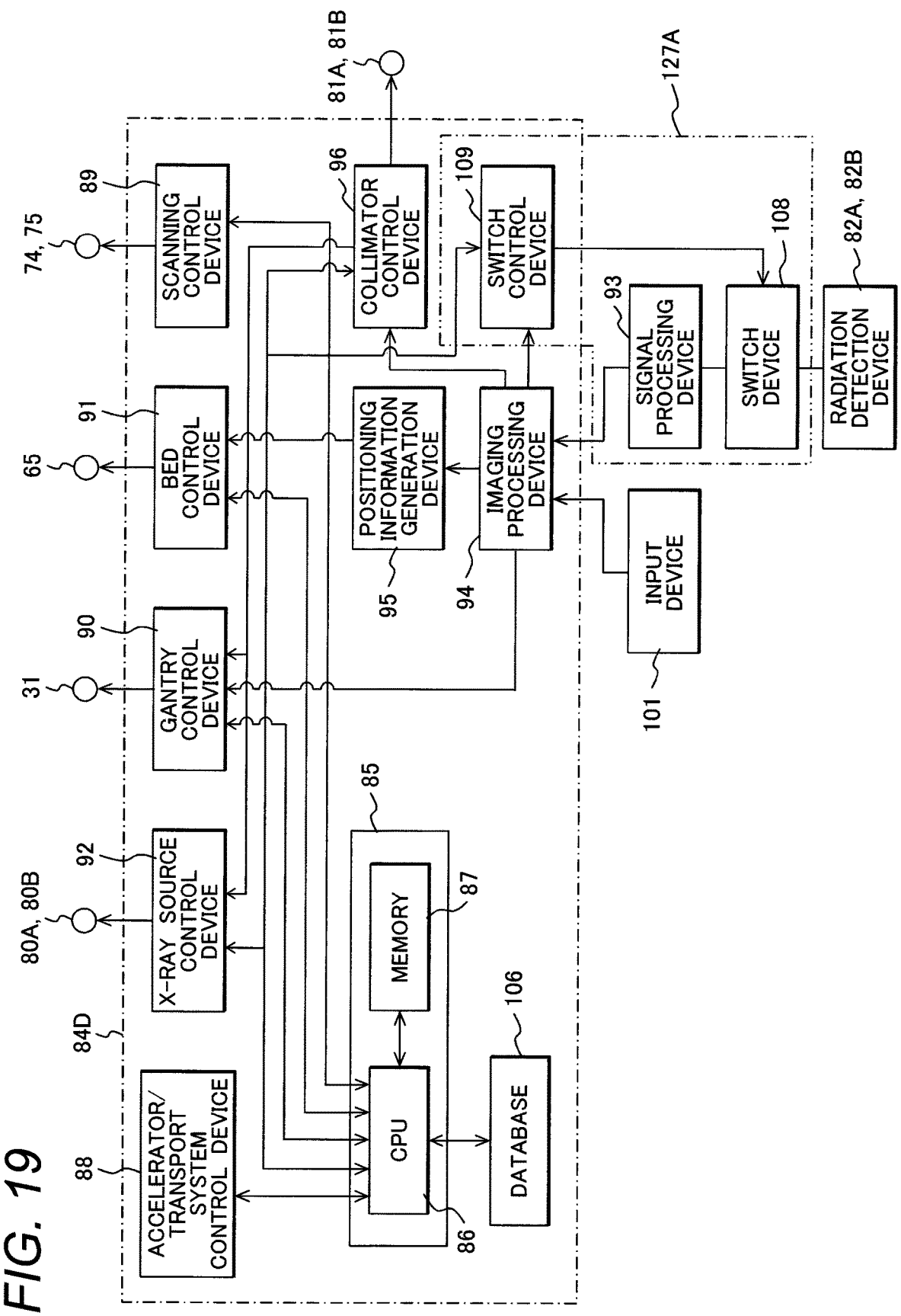
FIG. 19 is a diagram illustrating a detailed configuration of the control system shown in FIG. 1 according to another embodiment.
Figure 20:
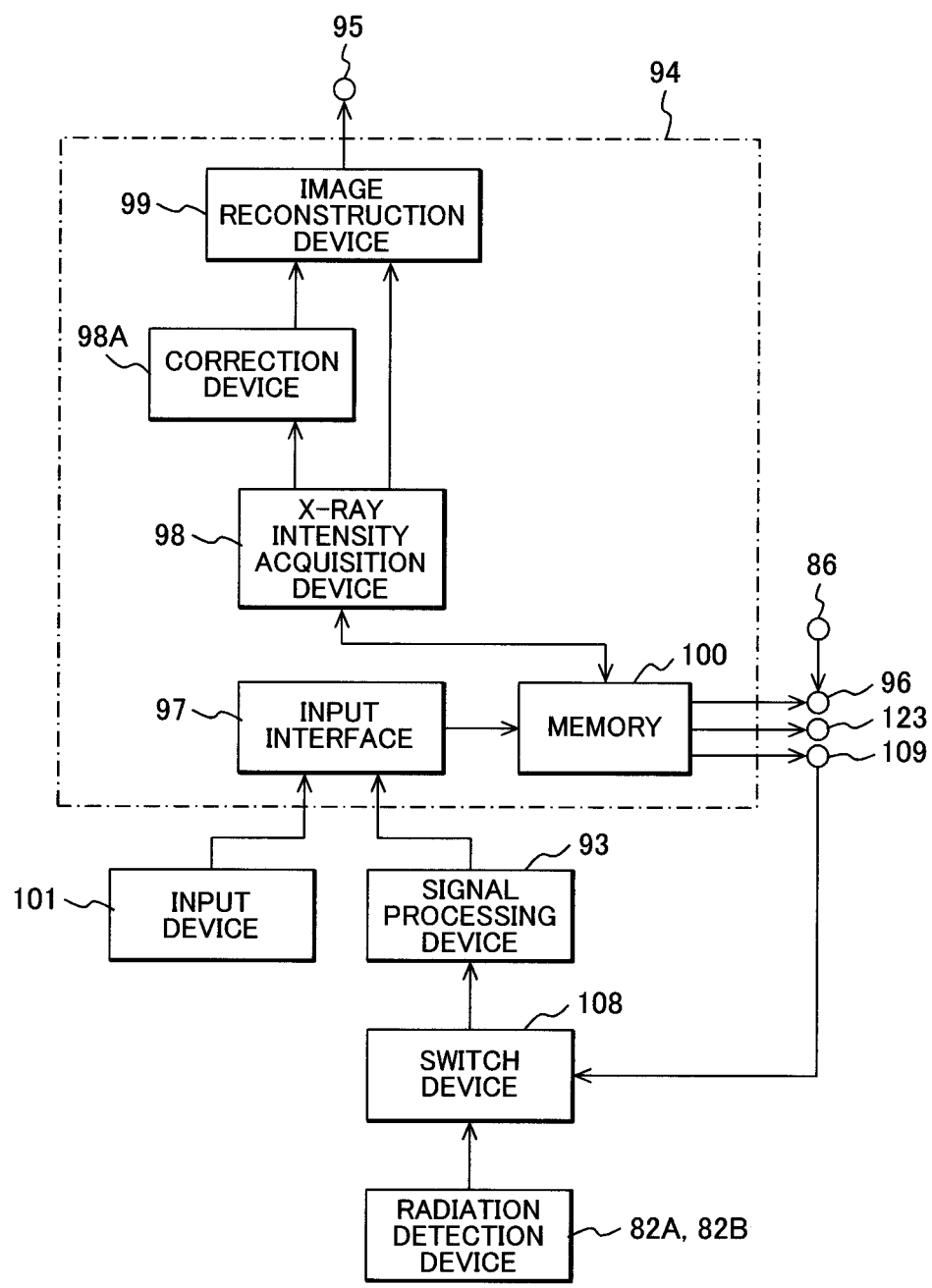
FIG. 20 is a diagram illustrating how the imaging processing device shown in FIG. 19 is connected to other devices.

Another embodiment of the control system will now be described with reference to FIG. 19. This control system 84D is obtained by adding a switch control device 109 to the earlier-described control system 84C. The other elements of the control system 84D are the same as those of the control system 84C. The imaging processing device 94 of the control system 84D, which is shown in FIG. 20, has the same configuration as the imaging processing device 94 of the control system 84C. When the control system 84D is used, a switch device 108 is disposed in the earlier-described particle beam therapy system 1. The switch device 108 is provided for each of the FPDs 82A, 82B. As described in Japanese Patent Application Laid-Open No. 2014-6235, the switch device 108 is configured by arranging many TFT switches (switching elements) (not shown) in a matrix form. Many radiation detection elements (not shown) of the FPD 82A, or more specifically, photodiodes, are connected to one switch device 108. The TFT switches disposed in the switch device 108 provided for the FPD 82A are connected to the radiation detection elements of the FPD 82A. Further, many radiation detection elements (not shown) of the FPD 82B, or more specifically, photodiodes, are connected to another switch device 108. The TFT switches disposed in the switch device 108 provided for the FPD 82B are connected to the radiation detection elements of the FPD 82B.

In each switch device 108, the many TFT switches arranged in a matrix form are connected to a signal wiring (not shown) for outputting the X-ray detection signals from the radiation detection elements and to a gate wiring (not shown) for conveying a control signal for turning ON or OFF the TFT switches. The TFT switches in the switch device 108 provided for the FPD 82A are connected to one signal processing device 93 through a signal wiring. Further, the TFT switches in this switch device 108 are connected to the switch control device 109 through a gate wiring. The TFT switches in the switch device 108 provided for the FPD 82B are connected to the other signal processing device 93 through a signal wiring. Further, the TFT switches in this switch device 108 are connected to the switch control device 109 through a gate wiring.

The aforementioned radiographic imaging apparatus may be applied to an X-ray therapy apparatus that treats a cancer-affected part in the head 79A or in the trunk 79B by irradiating X-rays onto the head 79A or the trunk 79B.

The particle beam therapy system 1 including the control system 84D and the switch device 108 in place of the control system 84C has a radiographic imaging apparatus that includes the X-ray sources 80A, 80B, the FPDs 82A, 82B, the collimators 81A, 81B, the signal processing device 93 (FIG. 19), the switch device 108 (FIG. 19), the imaging processing device 94 (FIG. 19), the switch control device 109, and the input device 101.

Functions of the control system 84D that differ from those of the control system 84C will now be described with reference to FIGS. 19 and 20.

First of all, it is assumed that the diseased part in the head 79A is to be treated by irradiating the diseased part with an ion beam. Before this treatment, current X-ray CT imaging is performed on the head 79A of the patient on the bed 65.

The small FOV information inputted from the input device 101 is stored in the memory 100. When the X-ray irradiation start command is inputted from the input device 101, the collimator control device 96 exercises control to drive the transport devices 122A-122D. This moves the diaphragm members 120A-120D as needed to adjust the size of the aperture 121.

The X-ray source control device 92 exercises control to let the X-ray sources 80A, 80B emit X-rays. At the same time, the second gantry control device 123B exercises control based on the small FOV information read from the memory 100 so that the rotary gantry 31 rotates from 0 degrees to 200 degrees while the X-rays are emitted from the X-ray sources. The X-rays 84A transmitted through the head 79A are mainly detected by the radiation detection elements in the small FOV area R1 of the FPD 82A, and the X-rays 84B transmitted through the head 79A are mainly detected by the radiation detection elements in the small FOV area R1 of the FPD 82B.

Based on the small FOV information read from the memory 100, the switch control device 109 outputs an ON signal through a gate wiring to all TFT switches of each switch device 108, which are connected to all radiation detection elements in the small FOV areas R1 of the FPDs 82A, 82B. This turns ON all the TFT switches of each switch device 108, which are connected to all the radiation detection elements in the small FOV areas R1. As a result, the X-ray detection signals outputted from all the radiation detection elements in the small FOV areas R1 of the FPDs 82A, 82B are inputted to the signal processing device 93 for each FPD through each TFT switch turned ON and through each signal wiring.

Each signal processing device 93 obtains X-ray intensity information about each radiation detection element in each of the FPDs 82A, 82B. A position code for each radiation detection element in the small FOV area R1 of the FPD 82A is attached to the X-ray intensity information, and a position code for each radiation detection element in the small FOV area R1 of the FPD 82B is attached to the X-ray intensity information. The resultant X-ray intensity information is stored in the memory 100.

The X-ray intensity acquisition device 98 inputs the X-ray intensity information, which is stored in the memory 100 when current X-ray CT imaging is performed on the head 79A. The whole X-ray intensity information stored in the memory 100 is obtained based on the X-ray detection signals outputted from all the radiation detection elements in the small FOV areas R1 of the FPDs 82A, 82B. Therefore, unlike the X-ray intensity acquisition device 98 in the control system 84C, the X-ray intensity acquisition device 98 in the control system 84D does not need to acquire, from the memory 100, the X-ray intensity information to which the position codes for all the radiation detection elements in the small FOV areas R1 are attached based on the small FOV information.

The correction device 98A, image reconstruction device 99, and positioning information generation device 95 in the control system 84D perform the same processes as the correction device 98A, image reconstruction device 99, and positioning information generation device 95 in the control system 84C. This calculates the movement amounts and rotation angle of the bed 65.

Upon completion of current X-ray CT imaging of the head 79A, the switch control device 109 outputs an OFF signal through a gate wiring to all TFT switches of each switch device 108, which are connected to all radiation detection elements in the small FOV areas R1 of the FPDs 82A, 82B. This turns OFF all the TFT switches of each switch device 108, which are connected to all the radiation detection elements in the small FOV areas R1.

As described earlier, the diseased part in the head 79A is positioned by moving the bed 65 based on the calculated movement amounts and rotation angle of the bed 65, and is then irradiated with an ion beam.

Before the diseased part in the trunk 79B is irradiated with an ion beam for treatment purposes, current X-ray CT imaging is performed on the trunk 79B having the diseased part.

The large FOV information inputted from the input device 101 is stored in the memory 100. As is the case with the current X-ray CT imaging of the head 79A, the size of the aperture 121 of each collimator 81A, 81B is adjusted, X-rays are irradiated onto the vicinity of the diseased part in the trunk 79B, and the rotary gantry 31 is rotated within a range of 0 to 360 degrees while the X-rays are irradiated. The X-rays 84A transmitted through the trunk 79B are mainly detected by the radiation detection elements in the large FOV area R2 of the FPD 82A, and the X-rays 84B transmitted through the trunk 79B are mainly detected by the radiation detection elements in the large FOV area R2 of the FPD 82B.

Based on the large FOV information read from the memory 100, the switch control device 109 outputs an ON signal through a gate wiring to all TFT switches of each switch device 108, which are connected to all radiation detection elements in the large FOV areas R2 of the FPDs 82A, 82B. This turns ON all the TFT switches of each switch device 108, which are connected to all the radiation detection elements in the large FOV areas R2. As a result, the X-ray detection signals outputted from all the radiation detection elements in the large FOV areas R2 of the FPDs 82A, 82B are inputted to the signal processing device 93 for each FPD through each TFT switch turned ON.

The X-ray intensity acquisition device 98 inputs the X-ray intensity information, which is stored in the memory 100 when current X-ray CT imaging is performed on the trunk 79B. The whole X-ray intensity information stored in the memory 100 is obtained based on the X-ray detection signals outputted from all the radiation detection elements in the large FOV areas R2 of the FPDs 82A, 82B. Therefore, unlike the X-ray intensity acquisition device 98 in the control system 84C, the X-ray intensity acquisition device 98 in the control system 84D does not need to acquire, from the memory 100, the X-ray intensity information to which the position codes for all the radiation detection elements in the large FOV areas R2 are attached based on the large FOV information.

The image reconstruction device 99 and positioning information generation device 95 in the control system 84D perform the same processes as the image reconstruction device 99 and positioning information generation device 95 in the control system 84C. This calculates the movement amounts and rotation angle of the bed 65.

Upon completion of current X-ray CT imaging of the trunk 79B, the switch control device 109 outputs an OFF signal through a gate wiring to all TFT switches of each switch device 108, which are connected to all radiation detection elements in the large FOV areas R2 of the FPDs 82A, 82B. This turns OFF all the TFT switches of each switch device 108, which are connected to all the radiation detection elements in the large FOV areas R2. Subsequently, the diseased part in the trunk 79B is irradiated with an ion beam.

The particle beam therapy system having the control system 84D and the switch device 108 includes an X-ray intensity information generation device 127A. The X-ray intensity information generation device 127A includes the switch device 108, the switch control device 109, and the signal processing device 93. The switch device 108 includes a switching element (TFT switch) that is connected to each radiation detection element in an FPD. The switch control device 109 outputs an ON signal to the switching elements connected respectively to the radiation detection elements in the small or large FOV area of the FPD based on the imaging mode information (either the small FOV information or the large FOV information) inputted from the input device 101. The signal processing device 93 generates the X-ray intensity information based on the X-ray detection signals from the radiation detection elements, which are outputted from the switching elements that are included in the switch device 108 and connected to the radiation detection elements by the ON signal from the switch control device 109. Based on an output signal from each radiation detection element in the FPD, the X-ray intensity information generation device 127A generates multiple pieces of X-ray intensity information about the small or large FOV area of the FPD.

The particle beam therapy system 1 to which the control system 84D is applied produces the same effects as the particle beam therapy system 1 to which the control system 84C is applied except that the former particle beam therapy system 1 does not produce the effects that the latter particle beam therapy system 1 produces by acquiring, from the memory 100, the X-ray intensity information about the associated FOV area based on the FOV information.

In the particle beam therapy system according to a later-described second, third, fourth, or fifth embodiment, the control system 84D and the switch device 108 may be used in place of the control system 84C.

Second Embodiment

The particle beam therapy system according to a second embodiment, which is another preferred embodiment of the present invention, will now be described with reference to FIG. 21.

The particle beam therapy system 1 according to the first embodiment uses the ion beam generation device 2 that includes the synchrotron accelerator 3. Meanwhile, the particle beam therapy system 1A according to the second embodiment uses an ion beam generation device 2A that includes a cyclotron accelerator 110.

Figure 21:
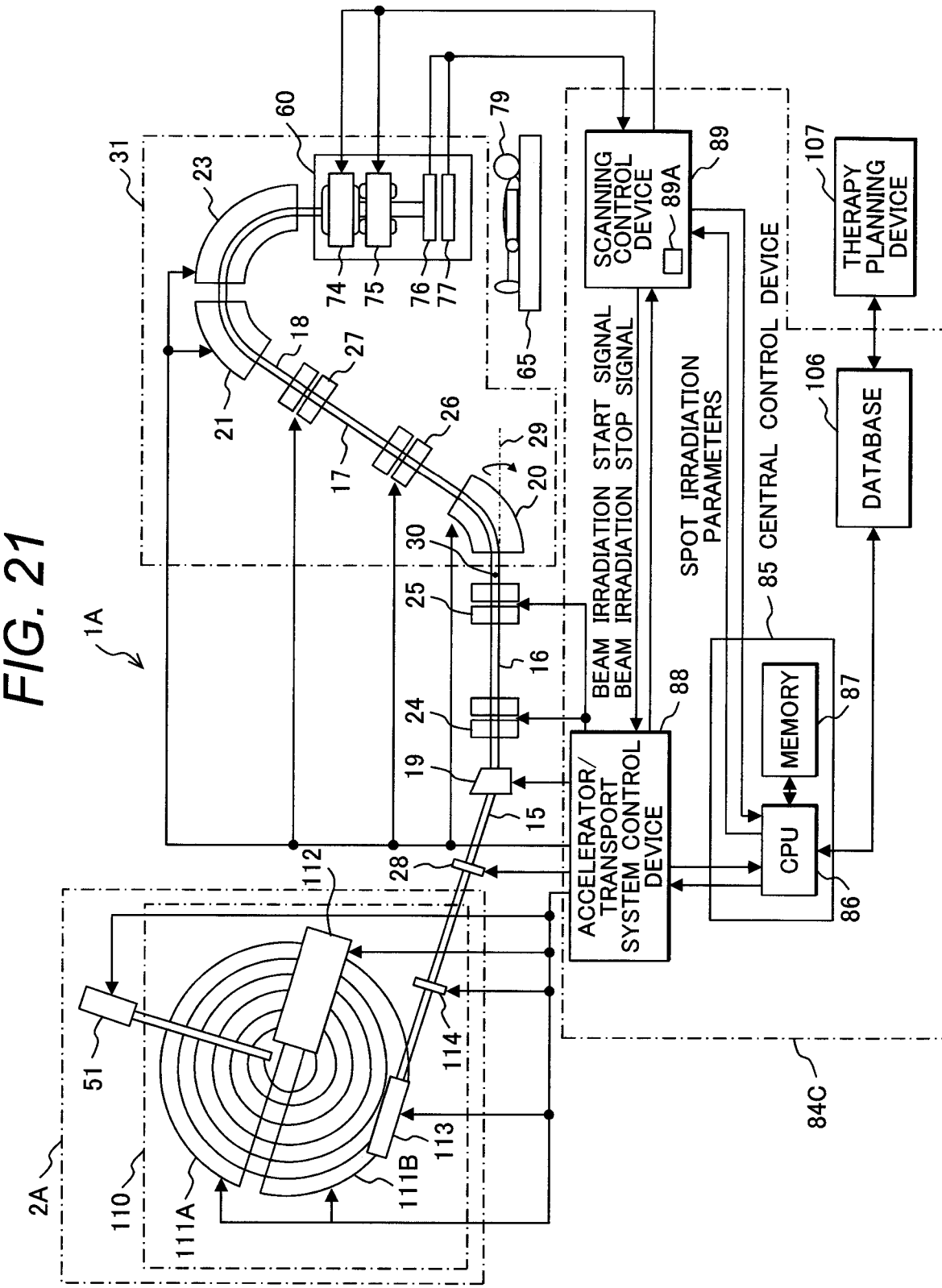
FIG. 21 is a diagram illustrating a configuration of the particle beam therapy system according to a second embodiment, which is another preferred embodiment of the present invention.

As illustrated in FIG. 21, the particle beam therapy system 1A includes the ion beam generation device 2A, the HEBT system 15, the GABT system 17, the rotary gantry 31, the irradiation device 60, and the control system 84C. The elements of the particle beam therapy system 1A are the same as those of the particle beam therapy system 1 except for the ion beam generation device 2A. Here, the ion beam generation device 2A, which is different from the ion beam generation device 2 in the particle beam therapy system 1, will be mainly described below.

The ion beam generation device 2A includes an ion source 51 and the cyclotron accelerator 110. The cyclotron accelerator 110 includes a circular vacuum vessel (not shown), deflection electromagnets 111A, 111B, a high-frequency acceleration device 112, and a septum electromagnet 113 for ejection. A vacuum duct connected to the ion source 51 is extended to the center of the vacuum vessel and connected to the vacuum vessel. An injection electrode (not shown) curved in the horizontal plane is positioned near an open end of the vacuum duct and disposed within the vacuum vessel. The deflection electromagnets 111A, 111B are semicircular in shape and disposed with their linear portions facing each other to cover the upper and lower surfaces of the vacuum vessel.

The septum electromagnet 113, which is disposed at an ion beam irradiation port of the vacuum vessel, is connected to the beam path 16 of the HEBT system 15. A degrader 114 having multiple metal plates is positioned between the septum electromagnet 113 and the shutter 28 and attached to the beam path 16. The degrader 114 is able to adjust the energy of an ion beam irradiated from the cyclotron accelerator 110 and is provided with multiple metal plates (not shown) differing in thickness. The metal plates are movable in a direction perpendicular to the beam path 16. The attenuation in energy of the ion beam passing through the beam path 16 is controlled by inserting one or more of the metal plates, which differ in length, into the beam path 16 in such a manner as to cross the beam path 16. As a result, the energy of the ion beam irradiated onto the diseased part in the head 79A or trunk 79B of the patient 79 can be changed as needed to irradiate the ion beam onto various layers existing in the depth direction of the diseased part.

As is the case with the first embodiment, the second embodiment permits the X-ray intensity acquisition device 98 to acquire multiple pieces of X-ray intensity information about the small FOV areas, which are included in the whole X-ray intensity information stored in the memory 100 and obtained based on the X-ray detection signals outputted from the radiation detection elements in the small FOV areas. Further, the second embodiment permits the X-ray intensity acquisition device 98 to acquire multiple pieces of X-ray intensity information about the large FOV areas, which are included in the whole X-ray intensity information stored in the memory 100 and are obtained based on the X-ray detection signals outputted from the radiation detection elements in the large FOV areas. The image reconstruction device 99 generates three-dimensional tomographic image information by using the multiple pieces of X-ray intensity information about the associated areas, which are acquired by the X-ray intensity acquisition device 98.

As is the case with the first embodiment, the second embodiment is configured so that the movable floor 39 includes the X-ray transmission plates 42A, 42B, and that the X-ray sources 80A, 80B and the collimators 81A, 81B are attached to the outer surface of the rotary drum 32, and further that the FPDs 82A, 82B are mounted on the irradiation device 60.

The particle beam therapy system 1A according to the second embodiment produces the same effects as the particle beam therapy system 1 according to the first embodiment.

Third Embodiment

Figure 22:
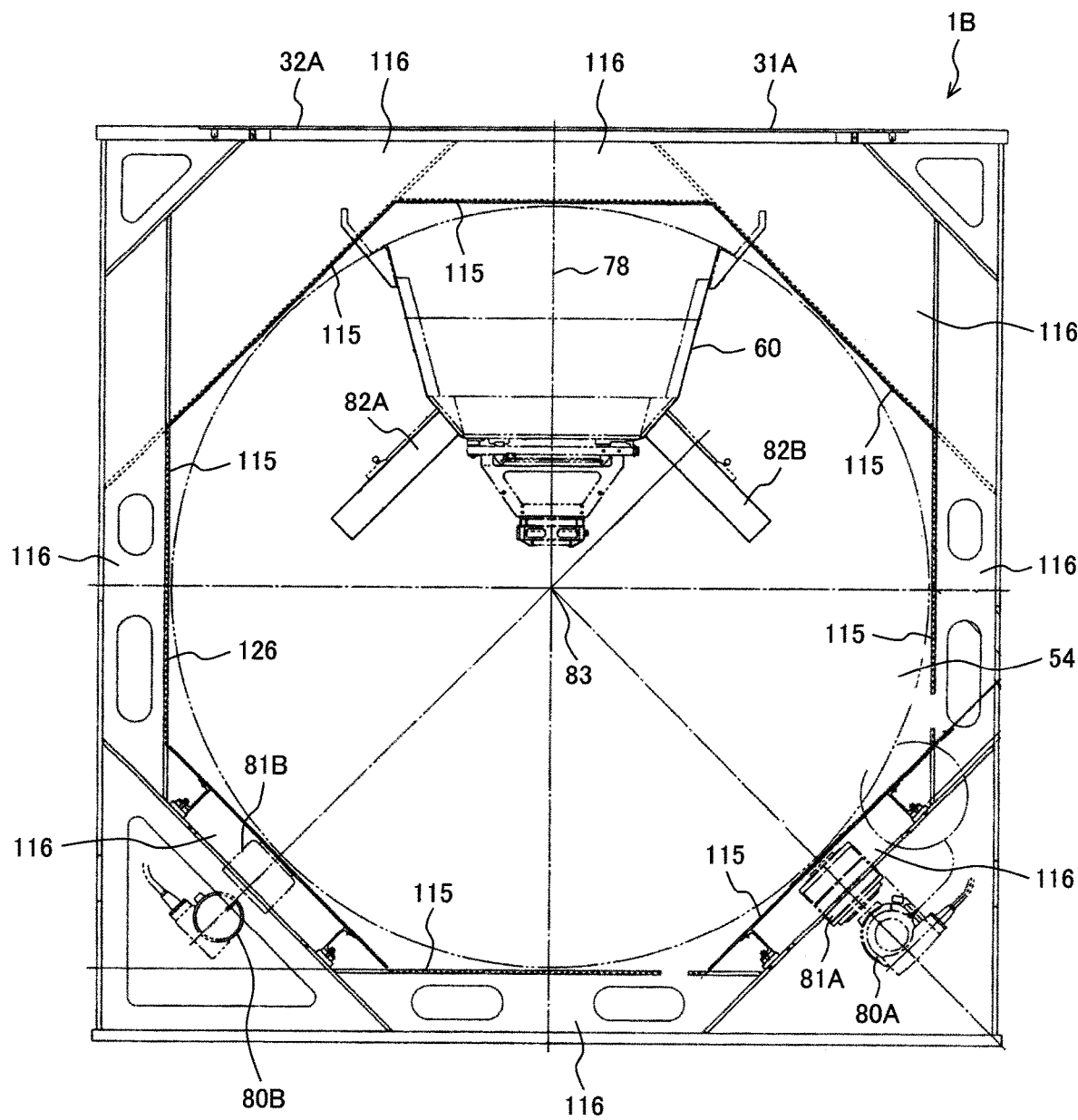
FIG. 22 is a diagram illustrating a configuration of the rotary gantry as viewed from a front ring in the particle beam therapy system according to a third embodiment, which is yet another preferred embodiment of the present invention.

The particle beam therapy system according to a third embodiment, which is yet another preferred embodiment of the present invention, will now be described with reference to FIG. 22.

The particle beam therapy system 1B according to the third embodiment is configured by replacing the rotary gantry 31 in the particle beam therapy system 1 according to the first embodiment with a rotary gantry 31A and by repositioning the X-ray sources 80A, 80B and collimators 81A, 81B. The other elements of the particle beam therapy system 1B are the same as those of the particle beam therapy system 1.

The rotary gantry 31A is configured by replacing the cylindrical rotary drum 32 of the rotary gantry 31 with a rectangular cylindrical rotary drum 32A having a square cross-section perpendicular to the rotation axis 29. Although not shown, the rotary drum 32A is similar to the rotary drum 32 in that the front ring 33 is attached to one end with the rear ring 34 attached to the other end. The front ring 33 and the rear ring 34 each have a circular outer surface. The front ring 33 and the rear ring 34 are each supported by the support rollers 37A that are rotatably disposed on the support devices 35A, 35B mounted on the floor 71 of the building. As is the case with the rotary gantry 31, the rotary gantry 31A is rotated by allowing the rotation device 52 to rotate the support rollers 37B disposed on the rear ring 34. The circumferential direction of the rotary gantry 31A denotes the circumferential direction of the outer surface of the front ring 33 (or the rear ring 34).

The rotary gantry 31A does not include the support roller 51A, the support rollers 51B, the ring rail drive device 55, and the therapy cage 38 with the movable floor 39, which are included in the rotary gantry 31. The rotary gantry 31A is configured by attaching eight frames 116 to the inner surface of the rotary drum 32A in such a manner as to form a regular octagon in a plane facing the central axis 29 of the rotary gantry 31A. Eight rectangular panels 115 extended in the direction of the central axis 29 of the rotary gantry 31A are positioned to face the inner surface of the rotary drum 32A and attached to the respective surfaces of the frames 116 that face the central axis 29 of the rotary gantry 31A. The eight panels 115 form a partition 126 that has a regular octagonal cross-section perpendicular to the rotation axis 29 of the rotary gantry 31A and defines the treatment room 54 within the rotary drum 32A. The irradiation device 60 mounted on the rotary drum 32A is extended into the treatment room 54 through the partition 126.

The FPD 82A is mounted on one lateral surface in the rotation direction of the irradiation device 60 in the treatment room 54, and the FPD 82B is mounted on the other lateral surface in the rotation direction of the irradiation device 60 in the treatment room 54. The one lateral surface of the irradiation device 60 on which the FPD 82A is mounted faces the other lateral surface of the irradiation device 60 on which the FPD 82B is mounted. The X-ray sources 80A, 80B are disposed between the rotary drum 32A and the panels 115 and attached to the inner surface of the rotary drum 32A with support members (not shown). The X-ray source 80A is disposed to face the FPD 82A, and the X-ray source 80B is disposed to face the FPD 82B. The collimator 81A is positioned between the X-ray source 80A and a panel 115, disposed in front of the X-ray source 80A, and attached to the above-mentioned support member that supports the X-ray source 80A. The collimator 81B is positioned between the X-ray source 80B and another panel 115, disposed in front of the X-ray source 80B, and attached to the above-mentioned support member that supports the X-ray source 80B.

When current X-ray CT imaging is performed on the diseased part in the head 79A or in the trunk 79B, X-rays emitted from the X-ray source 80A are transmitted through the X-ray transmission portion (formed, for example, of graphite) of a panel 115 that faces the X-ray source 80A, and irradiated onto the patient 79 on the bed 65, and the X-rays transmitted through the patient 79 are detected by the radiation detection elements of the FPD 82A. Meanwhile, X-rays emitted from the X-ray source 80B are transmitted through the X-ray transmission portion (formed, for example, of graphite) of a panel 115 that faces the X-ray source 80B, and irradiated onto the patient 79 on the bed 65, and the X-rays transmitted through the patient 79 are detected by the radiation detection elements of the FPD 82B.

As is the case with the first embodiment, the third embodiment permits the X-ray intensity acquisition device 98 to acquire multiple pieces of X-ray intensity information about the small FOV areas, which are included in the whole X-ray intensity information stored in the memory 100 and obtained based on the X-ray detection signals outputted from the radiation detection elements in the small FOV areas. Further, the third embodiment permits the X-ray intensity acquisition device 98 to acquire multiple pieces of X-ray intensity information about the large FOV areas, which are included in the whole X-ray intensity information stored in the memory 100 and obtained based on the X-ray detection signals outputted from the radiation detection elements in the large FOV areas. The image reconstruction device 99 generates three-dimensional tomographic image information by using the multiple pieces of X-ray intensity information about the associated areas, which are acquired by the X-ray intensity acquisition device 98.

The particle beam therapy system 1B according to the third embodiment produces the same effects as the particle beam therapy system 1 according to the first embodiment.

Fourth Embodiment

Figure 23:
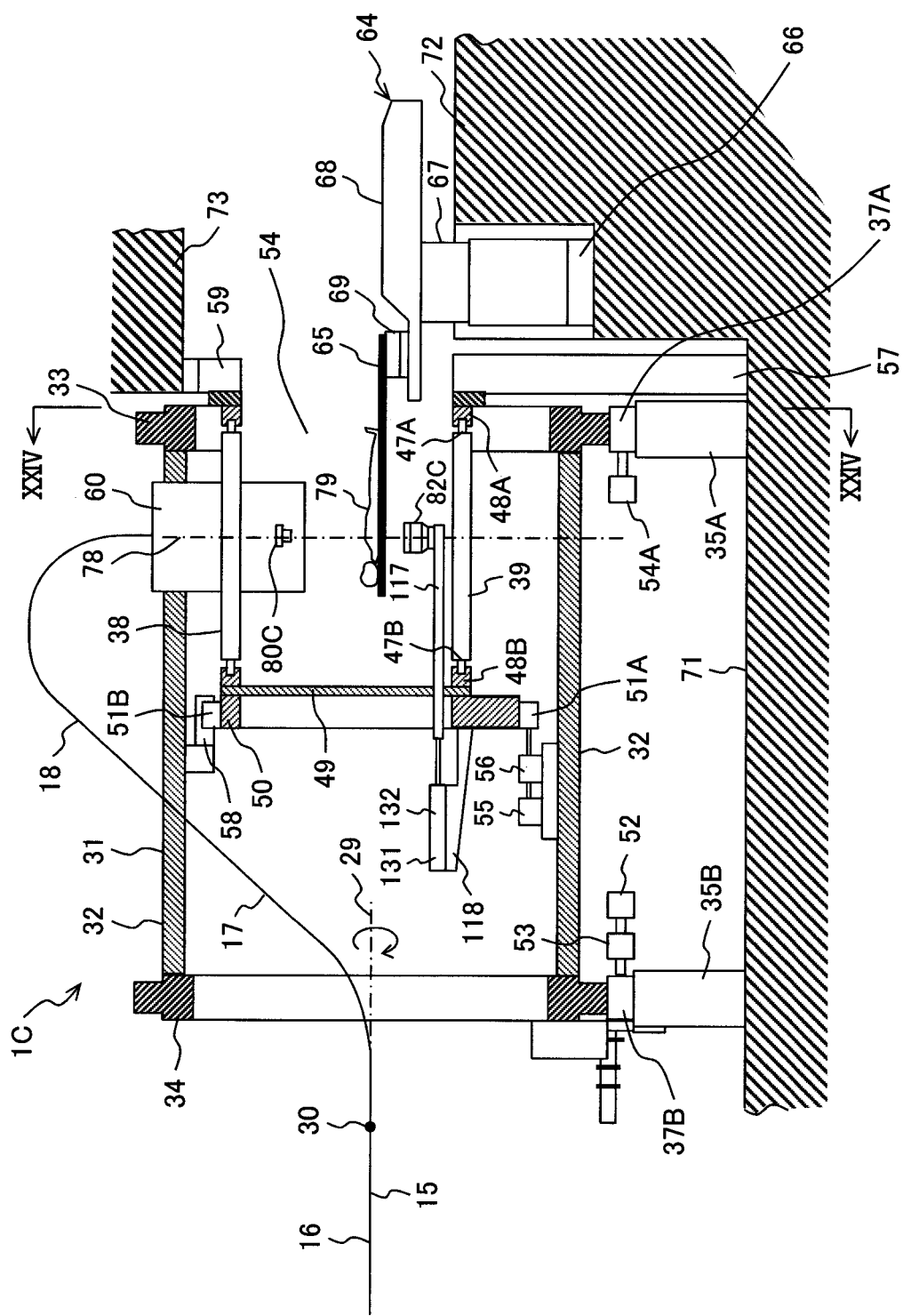
FIG. 23 is an enlarged longitudinal cross-sectional view of the rotary gantry in the particle beam therapy system according to a fourth embodiment, which is still another preferred embodiment of the present invention.
Figure 24:
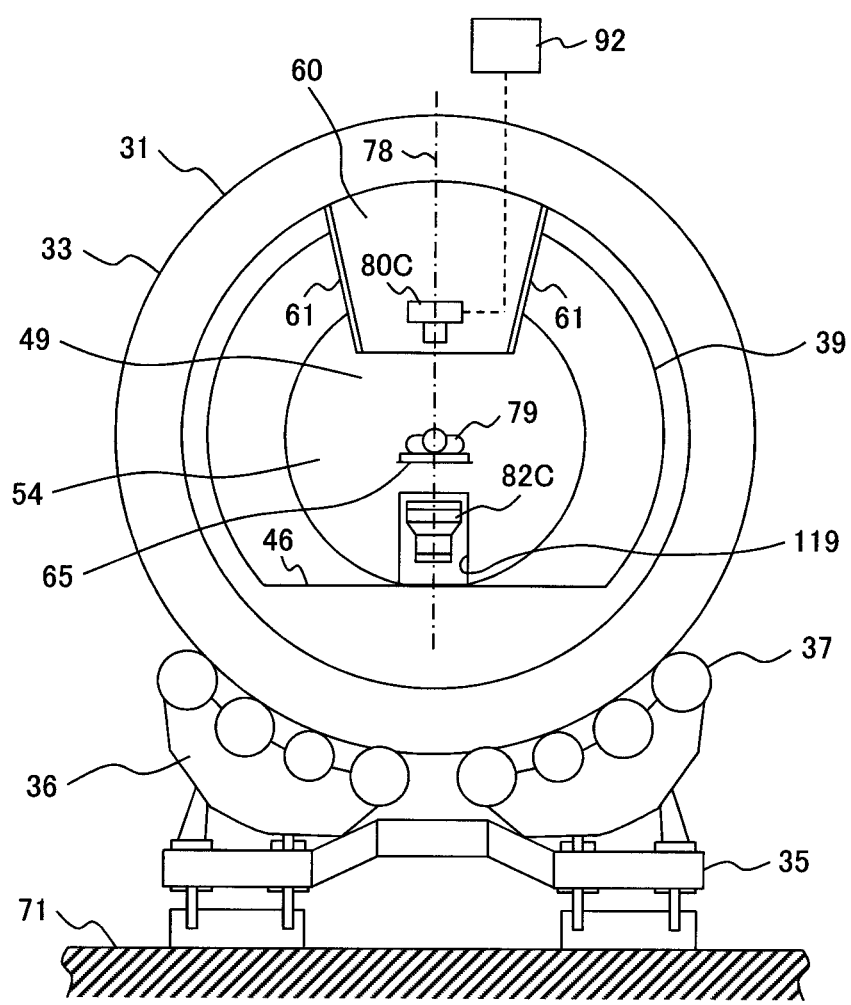
FIG. 24 is a cross-sectional view taken along line XXIV-XXIV of FIG. 23.

The particle beam therapy system according to a fourth embodiment, which is still another preferred embodiment of the present invention, will now be described with reference to FIGS. 23 and 24.

The particle beam therapy system 1C according to the fourth embodiment is configured by replacing the X-ray sources 80A, 80B in the particle beam therapy system 1 according to the first embodiment with an X-ray source 80C, by replacing the FPDs 82A, 82B with an FPD 82C, and by adding an FPD transport device 131. The other elements of the particle beam therapy system 1C are the same as those of the particle beam therapy system 1.

In the fourth embodiment, the X-ray source 80C is disposed in the irradiation device 60 and attached to an X-ray source transport device (not shown) mounted on the irradiation device 60. Although not shown, a collimator having the same configuration as the collimators 81A, 81B is positioned in the irradiation device 60, disposed in front of the X-ray source 80C, and attached to the X-ray source transport device. While the X-ray source 80C is oriented in a direction perpendicular to the central axis 78 of the irradiation device 60, the X-ray source transport device moves the X-ray source 80C and its collimator between a first position (the position of the central axis 78) and a second position. The first position is within an ion beam path in the irradiation device 60. The second position is outside the ion beam path.

The FPD transport device 131 includes a transport device 132 and a retaining member 117. The transport device 132 and the retaining member 117 are extended in the direction of the rotation axis of the rotary gantry 31. A guide member 118 is extended in the direction of the rotation axis of the rotary gantry 31, and attached to a surface of the rotary ring 50 that is positioned toward the rear ring 34. The transport device 132 is attached to the guide member 118 and supported by the guide member 118. The FPD 82C is attached to an end of the retaining member 117 and oriented toward the rotation axis 29 of the rotary gantry 31. The other end of the retaining member 117 is coupled to the transport device 132.

An aperture 119 is formed in the rear panel 49. The FPD 82C and the retaining member 117 pass through the aperture 119 and reach the inside of the treatment room 54.

When current X-ray CT imaging is to be performed on the head 79A or the trunk 79B, the transport device 132 is driven to move the FPD 82C to a position that is inside the movable floor 39, under the bed 65 on which the patient 79 lies, and directly below the diseased part. Additionally, the X-ray source transport device moves the X-ray source 80C and the collimator to the aforementioned first position. Subsequently, X-rays emitted from the X-ray source 80C are irradiated onto a radiation target (the vicinity of the diseased part of the head 79A or trunk 79B) of the patient 79. The X-rays transmitted through the patient 79 are detected by the radiation detection elements of the FPD 82C.

As is the case with the first embodiment, the fourth embodiment permits the X-ray intensity acquisition device 98 to acquire multiple pieces of X-ray intensity information about the small FOV areas, which are included in the whole X-ray intensity information stored in the memory 100 and obtained based on the X-ray detection signals outputted from the radiation detection elements in the small FOV areas. Further, the fourth embodiment permits the X-ray intensity acquisition device 98 to acquire multiple pieces of X-ray intensity information about the large FOV areas, which are included in the whole X-ray intensity information stored in the memory 100 and obtained based on the X-ray detection signals outputted from the radiation detection elements in the large FOV areas. The image reconstruction device 99 generates three-dimensional tomographic image information by using the multiple pieces of X-ray intensity information about the associated areas, which are acquired by the X-ray intensity acquisition device 98.

After completion of current X-ray CT imaging of the diseased part in the head 79A or the trunk 79B, the X-ray source 80C and the collimator are moved to the aforementioned second position in order to irradiate the diseased part with an ion beam, and the FPD 82C is moved toward the rear panel 49.

The particle beam therapy system 1C according to the fourth embodiment produces the same effects as the particle beam therapy system 1 according to the first embodiment. In the fourth embodiment, however, neither the position of the diseased part nor the effect of therapy provided by ion beam irradiation can be confirmed while the diseased part is irradiated with an ion beam.

Fifth Embodiment

The particle beam therapy system according to a fifth embodiment, which is an additional preferred embodiment of the present invention, will now be described with reference to FIG. 25.

The particle beam therapy system 1D according to the fifth embodiment is configured by replacing the X-ray source 80C in the particle beam therapy system 1C according to the fourth embodiment with the X-ray sources 80A, 80B and by replacing the FPD 82C with the FPDs 82A, 82B. Although not shown, the FPD transport device 131 is separately provided for each of the X-ray sources 80A, 80B and for each of the FPDs 82A, 82B, as is the case with the FPD 82C in the fourth embodiment. The X-ray source 80A is attached to an end of the retaining member 117 of one FPD transport device 131, and the X-ray source 80B is attached to an end of the retaining member 117 of one FPD transport device 131. Although not shown, the collimator 81A is disposed in front of the X-ray source 80A, and attached to an end of the retaining member 117 of an FPD transport device 131 that moves the X-ray source 80A. Although not shown, the collimator 81B is disposed in front of the X-ray source 80B, and attached to an end of the retaining member 117 of an FPD transport device 131 that moves the X-ray source 80B.

The FPD 82A is attached to an end of the retaining member 117 of another FPD transport device 131, and the FPD 82B is attached to an end of the retaining member 117 of a still another FPD transport device 131.

As is the case with the FPD transport device 131 in the fourth embodiment, each FPD transport device 131 in the fifth embodiment is supported by the guide member 118 attached to a surface of the rotary ring 50 that is positioned toward the rear ring 34.

Figure 25:
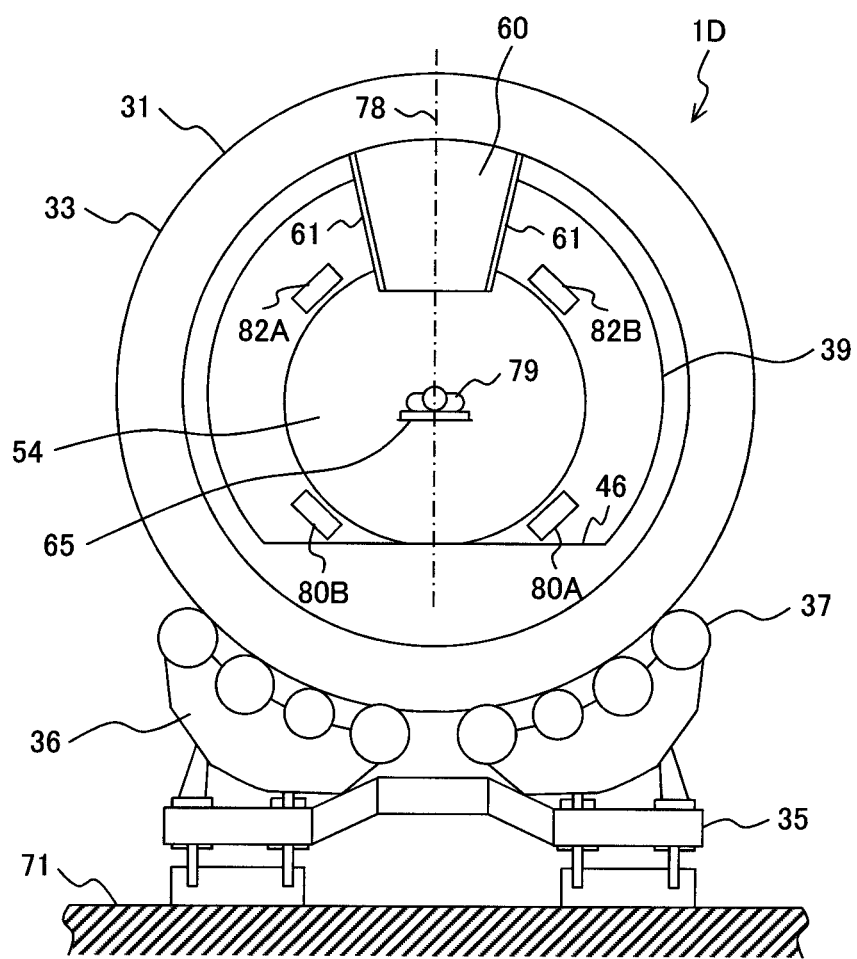
FIG. 25 is a diagram illustrating a configuration of the rotary gantry as viewed from the front ring in the particle beam therapy system according to a fifth embodiment, which is an additional preferred embodiment of the present invention.

When current X-ray CT imaging is to be performed on the diseased part in the head 79A or in the trunk 79B, the X-ray sources 80A, 80B and the FPDs 82A, 82B are positioned inside the movable floor 39, oriented by the associated FPD transport devices 131 to face the diseased part in the head 79A or trunk 79B of the patient 79 on the bed 65, and disposed at respective positions indicated in FIG. 25. In this instance, the X-ray source 80A and the collimator 81A face the FPD 82A, and the X-ray source 80B and the collimator 81B face the FPD 82B.

When current X-ray CT imaging is performed, X-rays emitted from the X-ray source 80A are passed through the aperture 121 of the collimator 81A and irradiated onto a radiation target of the patient 79. The X-rays transmitted through the patient 79 are detected by the radiation detection elements of the FPD 82A. X-rays emitted from the X-ray source 80B are passed through the aperture 121 of the collimator 81B and irradiated onto the radiation target of the patient 79. The X-rays transmitted through the patient 79 are detected by the radiation detection elements of the FPD 82B.

As is the case with the first embodiment, the fifth embodiment permits the X-ray intensity acquisition device 98 to acquire multiple pieces of X-ray intensity information about the small FOV areas, which are included in the whole X-ray intensity information stored in the memory 100 and obtained based on the X-ray detection signals outputted from the radiation detection elements in the small FOV areas. Further, the fifth embodiment permits the X-ray intensity acquisition device 98 to acquire multiple pieces of X-ray intensity information about the large FOV areas, which are included in the whole X-ray intensity information stored in the memory 100 and obtained based on the X-ray detection signals outputted from the radiation detection elements in the large FOV areas. The image reconstruction device 99 generates three-dimensional tomographic image information by using the multiple pieces of X-ray intensity information about the associated areas, which are acquired by the X-ray intensity acquisition device 98.

The particle beam therapy system 1D according to the fifth embodiment produces the same effects as the particle beam therapy system 1 according to the first embodiment.

DESCRIPTION OF REFERENCE NUMERALS 1, 1A, 1B, 1C, 1D . . . Particle beam therapy system
2, 2A . . . Ion beam generation device
3 . . . Synchrotron accelerator
4 . . . Beam duct
8 . . . High-frequency acceleration cavity
9 . . . High-frequency application device
15 . . . High-energy beam transport system
17 . . . Gantry beam transport system
31, 31A . . . Rotary gantry
32, 32A . . . Rotary drum
33 . . . Front ring
34 . . . Rear ring
38 . . . Radiotherapy cage
39 . . . Movable floor
42A, 42B . . . X-ray transmission plate
48A . . . Stationary ring rail
48B . . . Movable ring rail
54 . . . Treatment room
54A . . . Angle detector
60 . . . Irradiation device
61 . . . Connection member
62 . . . Guide rail
63A, 63B . . . Slide member
64 . . . Treatment table
65 . . . Bed
80A, 80B, 80C . . . X-ray source
81A, 81B . . . Collimator
82A, 82B, 82C . . . X-ray detection device (FPD)
84C, 84D . . . Control system 85 . . . Central control device
88 . . . Accelerator/transport system control device
89 . . . Scanning control device
90 . . . Gantry control device
91 . . . Bed control device
92 . . . X-ray source control device
94 . . . Imaging processing device
95 . . . Positioning information generation device
96 . . . Collimator control device
98 . . . X-ray intensity acquisition device
98A . . . Correction device
99 . . . Image reconstruction device
100 . . . Memory
101 . . . Input device
103A, 103B . . . Through hole
108 . . . Switch device
109 . . . Switch control device
110 . . . Cyclotron accelerator
115 . . . Panel
120A, 120B, 120C, 120D . . . Diaphragm member
122A, 122B, 122C, 122D . . . Transport device
125 . . . X-ray filter
126 . . . Partition
127, 127A . . . X-ray intensity information generation device

What is claimed is:

1. A particle beam therapy system comprising:
an accelerator that accelerates an ion beam;
a beam transport system that communicates with the accelerator and directs the ion beam from the accelerator;
a rotary gantry that rotates around a bed;
an irradiation device that is mounted on the rotary gantry to irradiate the radiation target with the ion beam injected from the beam transport system;
an X-ray generation device that is mounted on the rotary gantry;
a collimator that is disposed in front of the X-ray generation device to form an aperture through which X-rays from the X-ray generation device pass;
a radiation detection device that is mounted on the rotary gantry so as to face the X-ray generation device, disposed adjacent to the irradiation device and equipped with a plurality of radiation detection elements for detecting the X-rays passing through the aperture of the collimator;
an input device that inputs either first imaging mode information or second imaging mode information, the first imaging mode information concerning a first radiation target, the second imaging mode information concerning a second radiation target larger than the first radiation target;
an X-ray intensity information generation device that generates a plurality of pieces of X-ray intensity information about a selected field-of-view (FOV) area of the radiation detection device based on an output signal of each radiation detection element in the selected FOV area either when a first FOV area of the radiation detection device that is symmetrical in the circumferential direction of the rotary gantry with respect to a second straight line passing through a point of intersection between the radiation detection device and a first straight line passing through a rotation center of the rotary gantry from the X-ray generation device and extended in the direction of the rotation axis of the rotary gantry is selected based on the first imaging mode information inputted from the input device, or when a second FOV area of the radiation detection device that is not circumferentially symmetrical with respect to the second straight line passing through the point of intersection is selected based on the second imaging mode information inputted from the input device, wherein the point of intersection is the center of the first FOV area, and wherein the center of the first FOV area is positioned closer to the irradiation device than the center of the radiation detection device; and
an image reconstruction device that generates three-dimensional tomographic image information about a radiation target by using the plurality of pieces of X-ray intensity information generated by the X-ray intensity information generation device.

2. The particle beam therapy system according to claim 1, wherein the X-ray intensity information generation device includes
a signal processing device that generates the X-ray intensity information based on output signals from the radiation detection elements included in the radiation detection device,
a memory that stores the X-ray intensity information generated by the signal processing device, and
an X-ray intensity acquisition device that acquires, from the memory, the X-ray intensity information that is obtained based on the output signals from the radiation detection elements in either the first or second FOV area of the radiation detection device, whichever is selected based on the imaging mode information inputted from the input device.

3. The particle beam therapy system according to claim 1, wherein the X-ray intensity information generation device includes
a switch device that includes a switching element connected to each of the radiation detection elements in the radiation detection device,
a switch control device that outputs an ON signal to the switching element connected to each radiation detection element in either the first or second FOV area of the radiation detection device, whichever is selected based on the imaging mode information inputted from the input device, and
a signal processing device that generates the X-ray intensity information based on the output signal of the radiation detection element outputted through the switching element inputted the ON signal from the switch control device.

4. The particle beam therapy system according to claim 1, wherein the collimator includes a plurality of movable diaphragm members for changing the size of the aperture, one of the diaphragm members being provided with an X-ray filter for covering the aperture from a side toward the radiation detection device.

5. The particle beam therapy system according to claim 2, further comprising:
a correction device that corrects a plurality of pieces of X-ray intensity information based on the amount of offset when the X-ray intensity information generation device generates the plurality of pieces of X-ray intensity information about each of the first and second FOV areas, the offset being a distance between the center of the radiation detection device and the point of intersection.

6. The particle beam therapy system according to claim 1, further comprising:
a first gantry control device that rotates the rotary gantry until a central axis of the irradiation device agrees with irradiation direction information about the ion beam, the irradiation direction information being set in a therapy plan; and a second gantry control device that changes the range of rotation of the rotary gantry based on the imaging mode information inputted from the input device when the X-rays are to be irradiated onto the radiation target.

7. The particle beam therapy system according to claim 1, further comprising:

a therapy cage that is disposed in the rotary gantry and provided with a surrounding member that is formed by coupling a plurality of footboard members to move along a track formed to include an arc portion and a horizontal portion in communication with the arc portion;

wherein the X-ray generation device is disposed outside the surrounding member and mounted on the rotary gantry;

wherein the radiation detection device is disposed inside the surrounding member and mounted on the irradiation device; and wherein the surrounding member includes an X-ray transmission member, the X-ray transmission member being coupled to the neighboring footboard members, and being disposed between the X-ray generation device and the radiation detection device to transmit the X-rays from the X-ray generation device.

8. The particle beam therapy system according to claim 7, wherein the X-ray generation device is disposed outside the rotary gantry and mounted on the outer surface of the rotary gantry, and wherein an X-ray passage hole is formed to face the X-ray generation device on the rotary gantry.

9. The particle beam therapy system according to claim 7, further comprising:

a pair of connection members that is disposed on the irradiation device to connect opposite ends of the surrounding member and a pair of opposing lateral surfaces of the irradiation device in such a manner as to permit the opposite ends of the surrounding member and the opposing lateral surfaces of the irradiation device to move in a radial direction of the rotary gantry.

10. The particle beam therapy system according to claim 9, wherein the connection members each include a guide member that is attached to a lateral surface of the irradiation device and extended in the radial direction of the rotary gantry, and a slide member that is attached to each of the ends of the surrounding member and movably attached to the guide member.

11. The particle beam therapy system according to claim 1, wherein the rotary gantry includes a rectangular cylindrical rotary drum, wherein a tubular partition having a regular octagonal cross-section perpendicular to the rotation axis of the rotary gantry is disposed in the rotary drum and attached to the inner surface of the rotary drum, and wherein the X-ray generation device and the collimator disposed in front of the X-ray generation device are disposed between the partition and the rotary drum.

12. The particle beam therapy system according to claim 7, comprising:

the X-ray generation device disposed in the irradiation device;

a first transport device that moves the X-ray generation device between a first position and a second position, the first position being inside a beam path through which the ion beam in the irradiation device passes, the second position being outside the beam path; and a second transport device that moves the radiation detection device mounted on the second transport device to a position facing the irradiation device inside the surrounding member.

* * * * *